United States Patent [19]
Klinzing et al.

[11] Patent Number: 5,697,158
[45] Date of Patent: Dec. 16, 1997

[54] ORTHOPEDIC SURGICAL DEVICE HAVING A ROTATABLE PORTION AND LOCK

[75] Inventors: William P. Klinzing, St. Paul; Martin P. Babcock, Woodbury, both of Minn.

[73] Assignee: Minnesota Mining and Manufacturing Company, St. Paul, Minn.

[21] Appl. No.: 576,470

[22] Filed: Dec. 21, 1995

[51] Int. Cl.$^6$ ................................................ A61B 17/14
[52] U.S. Cl. ........................ 30/166.3; 30/329; 30/340; 606/82; 606/176
[58] Field of Search ........................ 173/29; 408/20; 279/144; 606/80, 79, 82, 104, 167, 176, 177, 178; 30/12, 166.3, 329, 340, 392, 393, 501, 502, 362, 363, 376, 377; 83/597, 601, 607, 608, 698.11, 698.31, 698.41, 699.11, 699.21, 699.31, 699.41, 699.51, 699.61, 747, 750; 403/325–327

[56] References Cited

U.S. PATENT DOCUMENTS

| | | |
|---|---|---|
| 2,436,372 | 2/1948 | Avery . |
| 2,740,406 | 4/1956 | Tofflemire ................................. 606/79 |
| 2,851,287 | 9/1958 | Tangard . |
| 3,016,759 | 1/1962 | Fletcher . |
| 3,120,133 | 2/1964 | Diener et al. . |
| 3,127,786 | 4/1964 | Wooley . |

(List continued on next page.)

FOREIGN PATENT DOCUMENTS

| | | |
|---|---|---|
| 0 324 638 | 1/1989 | European Pat. Off. . |
| WO 92/11112 | 9/1992 | WIPO . |

OTHER PUBLICATIONS

Product Brochure entitled: "Sagittal Saw Attachment", by 3M, (2 pages). This brochure describes a device sold in the U.S. more than one year prior to the filing date of the present application.

Product Brochure entitled: "Powered Instrumentation For Large Bone Surgery, The Power of Choice" by Stryker Instruments (15 pages). This brochure describes devices believed to have been sold in the U.S. more than 1 year prior to the filing date of the present case.

(List continued on next page.)

*Primary Examiner*—Rinaldi I. Rada
*Assistant Examiner*—Boyer Ashley
*Attorney, Agent, or Firm*—Gary L. Griswald; Walter N. Kirn; Jeffrey J. Hohenshell

[57] ABSTRACT

The present invention comprises a module for a surgical driver of the type having a handle and a barrel with an axis. The module comprises a releasable attachment mechanism for releasably attaching the module to the surgical driver, a tool mounting mechanism for releasably receiving an orthopedic surgical tool, and a rotational orientation mechanism for orienting the tool mounting mechanism in a plurality of angular positions about an axis of the barrel. The device includes a releasable locking mechanism for releasably locking the rotational orientation mechanism in one of a plurality of discrete angular positions about the axis of the barrel. The releasable locking mechanism has a locking member movable between lock and release positions. A spring biases the locking mechanism toward the lock position. The novel locking mechanism of the present invention may also be used in non-modular devices.

26 Claims, 12 Drawing Sheets

U.S. PATENT DOCUMENTS

| | | |
|---|---|---|
| 3,136,563 | 6/1964 | Swanson et al. . |
| 3,432,194 | 3/1969 | Garnier ............................. 403/325 X |
| 3,554,197 | 1/1971 | Dobbie . |
| 3,640,280 | 2/1972 | Slanker et al. . |
| 3,734,515 | 5/1973 | Dudek ................................. 173/29 X |
| 3,752,241 | 8/1973 | Bent . |
| 3,754,330 | 8/1973 | Anderson et al. ................ 30/392 X |
| 3,841,335 | 10/1974 | Tarsitano . |
| 3,876,015 | 4/1975 | Kivela ................................. 173/170 |
| 3,986,512 | 10/1976 | Walliser . |
| 4,008,720 | 2/1977 | Brinckmann et al. . |
| 4,069,723 | 1/1978 | Payerle . |
| 4,109,735 | 8/1978 | Bent . |
| 4,289,131 | 9/1981 | Mueller . |
| 4,367,971 | 1/1983 | Coren ................................. 403/327 X |
| 4,649,769 | 3/1987 | Venable . |
| 4,728,020 | 3/1988 | Green et al. . |
| 4,728,876 | 3/1988 | Mongeon et al. . |
| 4,736,742 | 4/1988 | Alexson et al. . |
| 4,768,504 | 9/1988 | Ender ................................. 606/177 |
| 4,819,334 | 4/1989 | Mongeon .......................... 30/393 |
| 4,949,463 | 8/1990 | Chen ................................... 30/500 |
| 4,961,421 | 10/1990 | Muller . |
| 5,201,749 | 4/1993 | Sachse et al. . |
| 5,230,154 | 7/1993 | Decker et al. .................... 30/329 X |
| 5,263,972 | 11/1993 | Evans et al. . |
| 5,265,343 | 11/1993 | Pascaloff . |
| 5,340,129 | 8/1994 | Wright .............................. 30/392 X |
| 5,439,472 | 8/1995 | Evans et al. . |
| 5,456,135 | 10/1995 | Li ...................................... 403/325 X |
| 5,464,300 | 11/1995 | Craninich ........................ 403/327 X |
| 5,553,675 | 9/1996 | Pitzen et al. ..................... 173/217 |

OTHER PUBLICATIONS

Product Brochure entitled: "System 2000 Heavy Duty Battery Powered Instruments", by Stryker Instruments, (11 pages). This brochure describes devices which are believed to have been sold in the U.S. more than one year prior to the filing date of the present invention.

Product Brochure: "The Air Driver II from 3M", by 3M (2 pages). This brochure describes a device that was sold in the U.S. more than one year prior year to the filing date of the present invention.

"Mini Driver™ Air Instrument System" from 3M, 4 page brochure, 1975.

Cordless Sagittal Saw from Dyonics, 2 page brochure, Feb. 1, 1984.

Product brochure entitled: "Maxion™ Cordless Powered Instrument System, Assembly, Operation and Maintenace", by 3M HealthCare (6 pages) pp. 1, 3, 4, and 15–16 from a brochure describing a prior art prodcut sold more than 1 year prior to the present filing date.

Hall® Versipower™ Dual Power Orthopaedic Instruments, by Zimmer, 1989 (6 pages). Describes a prior art device that was on sale in the U.S. more than 1 year prior to the present filing date.

Instruction Manual entitled: "The Hall® Orthair™ System" by Zimmer USA, (12 pages). This brochure describes prior art devices that were for sale in the U.S. more than 1 year prior to the filing date of the present case.

Product brochure entitled, "System II OrthPower 90 Battery Surgical Instruments", by Stryker® (16 pages). This brochure describes a prior art device that was on sale in the U.S. more than 1 year prior to the filing date of the present application.

Product brochure entitled, "Maxion™ Cordless Powered Instrument System", by 3M Health Care, (31 pages). This brochure describes a prior art device which was on sale in the U.S. more than 1 year prior to the filing date of the present application.

Product brochure entitled: "Maxion™ Cordless Powered Instruments System", by 3M Health Care (4 pages).

Product brochure entitled: "Maxi–Driver™ 3 Powered Surgical Instrument System, Assembly, Operation and Maintenance" by 3M Health Care (47 pages), 1993.

Product brochure entitled: "System 2000 Battery Powered Instruments" by Stryker Instruments, (15 pages), Jan. 1993.

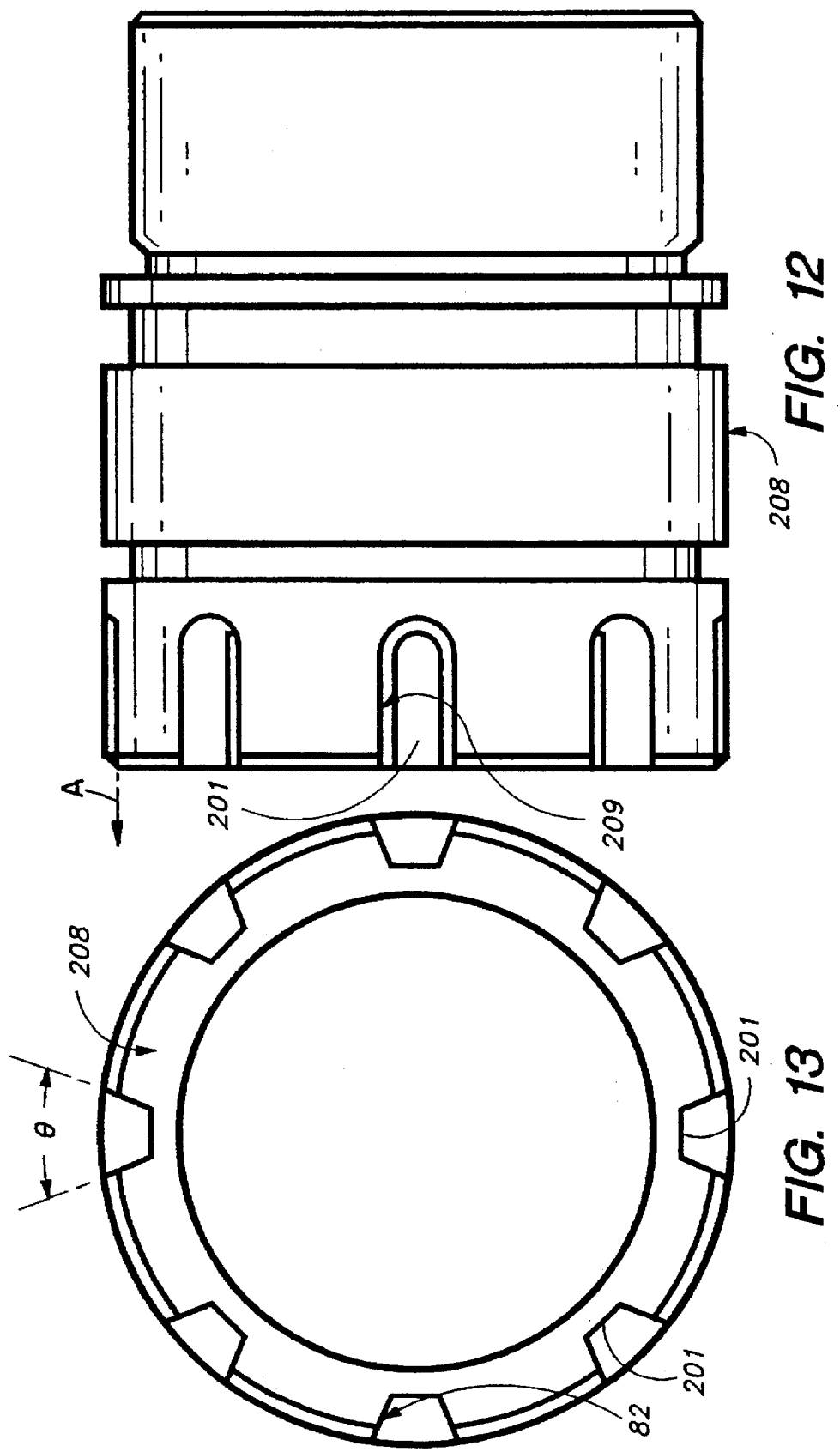

ORTHOPEDIC SURGICAL DEVICE HAVING A ROTATABLE PORTION AND LOCK

TECHNICAL FIELD

This invention relates to orthopedic surgical devices having rotatable portions with locking mechanisms and more particularly to modules for use with surgical devices that have rotatable portions that are adapted to be locked in one of a plurality of orientations.

BACKGROUND

Orthopedic surgery presents a particularly difficult challenge for a surgeon. A typical orthopedic surgical procedure is a delicate, yet physically demanding task. When bone is to be removed or modified, powerful devices are used to cut or otherwise modify the tough material of bone, yet considerations are made to the accurate placement of the surgical procedure (e.g. cuts), to the presence of adjacent soft tissues, and to a degree of convenience so that the surgical incision can be closed as soon as possible.

Orthopedic drive assemblies are well known in the art. Cordless battery powered drive assemblies for driving orthopedic surgical instruments are described in U.S. Pat. Nos. 3,734,207; 4,050,528; 4,091,880; 4,441,563; 4,641,076; 4,728,876 and 5,080,983. Orthopedic drive assemblies may be adapted for various orthopedic procedures such as drilling, screwing, reaming, wire driving, pinning and sawing (both reciprocating and sagittal). A particularly useful orthopedic drive device is known as an oscillating or sagittal type saw. In such a saw, the cutting teeth are arranged on the distal end of an elongated blade which is oscillated generally about a fixed point along its longitudinal axis. In order to improve the convenience of the device, it is known to provide such a saw in the form of a pistol-shaped, hand held tool with barrel and hand grip (or handle) portions. The saw blade is mounted on a blade mount at a distal end of the barrel portion of the saw, and the blade mount is moved by a drive extending from a motor. Saw blades are shown, for example, in U.S. Pat. No. 4,386,609 and U.S. patent application Ser. No. 08/469,807 (the entire contents of which are herein incorporated by reference).

Over the years pistol-shaped orthopedic drive devices have developed to include features that allow the mounting assembly for the tool (e.g. a saw blade) to be placed in a plurality of orientations relative to the proximal portion of the barrel portion of the handpiece. A feature which allows the mounting mechanism for a saw blade to be placed in a plurality of orientations relative to the barrel portion of the handpiece contributes to the accurate, precise placement of the orthopedic tool (e.g. saw blade), and to the comfort of the grip perceived by the surgeon. It is also considered to be more convenient for the surgeon. For example, a surgeon may need to cut bone that is situated in a remote, minimally exposed location. Rather than requiring the surgeon to place himself or herself in an awkward orientation or to use an unnatural hand position, the orientation of the saw blade relative to the rest of the device is simply changed. These devices afford a comfortable grip and operating position regardless of the blade angle required by the surgical procedure. Such orthopedic devices include devices referred to in the art as rotatable saws.

Rotatable saw designs include modular and non-modular designs. In a modular device, a single drive assembly or handpiece may be utilized to drive a plurality of different orthopedic surgical tools such as reciprocating or oscillating saw blades, drill bits and wires by utilizing different tool modules with different tool mounts. In a non-modular system, a different drive device or handpiece is typically required to drive the various diverse surgical tools. Non-modular designs of orthopedic saws include: a) sagittal saw model number 2108, available from Stryker of Kalamazoo, Mich., b) Versipower orthopedic oscillator saw (Model No. 5048-02) available from Hall/Zimmer of Carpinteria, Calif., c) Cordless Sagittal Saw (model no. 2855) generally available from Dyonics of Andover Md., and d) Versipower orthopedic reciprocating saw. While each of these saws include a feature that allows the mounting mechanism for the saw blade to be positioned in a plurality of orientations relative to the barrel portion of the device, the designs leave room for enhancement.

U.S. Pat. No. 5,263,972 discloses a non-modular saw which appears similar to the sagittal saw (model number 2108) available from Stryker. The 2108 sagittal saw includes an assembly in the barrel portion of the device that includes a housing piece having eight longitudinally extending cylindrical holes situated in positions equally spaced about a longitudinal axis of the barrel portion of the saw. The device also includes an element with two longitudinally extending cylindrical pins that are adapted to fit into the cylindrical holes to lock the saw blade mounting mechanism (and the mounted saw blade) in a preselected orientation relative to the barrel portion of the device. The pins are spring biased into the holes by a spring that provides a biasing force along the longitudinal axis of the barrel portion of the device. To rotate the saw about the axis of the housing piece with eight holes and relative to the barrel portion of the device, a user pulls on the distal end of the barrel portion longitudinally (distally) away from the rest of the barrel portion until the spring bias on the pins is overcome and the pins are removed from a first pair of the eight holes. With the pins removed from the holes, the saw blade and mounting assembly (and the pins) are free to be rotated relative to the rest of the barrel portion (e.g. the eight holes). When the desired orientation is selected, the user releases the distal end of the barrel portion and allows the pins to enter a different pair of the eight holes under the bias of the spring.

While the mounting assembly of the 2108 sagittal saw allows the saw blade mounting mechanism to be placed in a plurality of positions relative to the barrel portion of the device, it leaves much to be desired. Because two pins are utilized, the design is believed to be difficult to manufacture. In particular, it is believed that the tolerances for the size of the pins and holes and the circumferential location of the pins and holes should be carefully monitored. A loose fit between the parts may easily result, unless careful attention is paid to these tolerances. The tolerance issue is accented when it is considered that the amount of vibration encountered by a surgeon during a typical orthopedic surgical procedure is significant. Indeed, hand fatigue is a problem associated with many existing drive assemblies as well as a general difficulty in maneuvering the device during some surgical procedures. All components of the device are typically subject to the intense vibration at least to some degree, including the assembly that allows the orientation of the mounting mechanism for the saw blade to be changed.

It is believed that the assembly of the 2108 sagittal saw is susceptible to excessive wear which can result in unacceptable, loose fits between the various parts (e.g. the pins and holes). Loose fits between parts such as the pins and holes may result in a device that allows the distal portion of the barrel portion to unduly vibrate relative to the rest of the barrel portion, thereby potentially adversely affecting the overall accuracy and precision of the instrument. Any adverse affect on the accuracy of a surgical device is troubling, particularly for devices used during delicate orthopedic procedures where only the highest standard of quality is tolerated.

Another problem associated with the design of the 2108 sagittal saw is that some users may find it difficult to reorient the saw blade. In particular, the design encourages a user to overcome the spring bias and to rotate the distal end of the barrel portion (the saw blade mounting mechanism) with the same hand. This complicated hand movement may be difficult for some users, particularly when it is considered that this hand movement may be performed close to a sharp saw blade.

An example of a prior art modular orthopedic oscillating saw comprises the pneumatically driven Mini-Driver drive device with a module known as the K-120 Sagittal Saw Attachment available from the Minnesota Mining and Manufacturing Co. (3M) of St. Paul, Minn. With such a device, the saw blade could be mounted in a plurality of positions relative to the proximal end of the barrel portion of the device. However, in order to change the orientation of the saw blade relative to the barrel, a user is required to remove pins on the module from lockable slots on the barrel and then reattach the pins of the module in the modified orientation. As a result, modifying the orientation of the saw blade relative to the barrel portion is not a simple task. With some users (particularly those unaccustomed to the drive device), the task of modifying the orientation of the saw blade may be time consuming and cumbersome, thereby unduly extending the time required for the surgical procedure and the complexity of the operation.

Another example of a prior art modular orthopedic oscillating saw comprises the Maxi-Driver 3 powered surgical instrument system with an oscillating saw attachment (G220) available from Minnesota Mining and Manufacturing Co. (3M) of St. Paul, Minn. FIG. 12 of U.S. Pat. No. 4,736,742 discloses a similar device (see column 9, lines 30–43). Improvements were made to the device described in U.S. Pat. No. 4,736,742 in an attempt to provide a feature that would lock the mount for the saw blade in a plurality of positions relative to the barrel portion of the device. First, a sleeve element was provided with a plurality of longitudinally extending slots. A releasable engagement mechanism was provided to engage the slots in an effort to hold the saw blade mount in a preselected position relative to the barrel portion of the device. This mechanism was not found to satisfactorily hold the saw blade mount in position relative to the barrel portion of the device, as the engagement mechanism could become dislodged from the slots.

An attempt was made to improve the device by supplying a threaded lockdown collar or ring. Complementary threads on the barrel portion of the module and the lockdown collar enabled the lockdown collar to be screwed over the engagement member/slot assembly to enhance the engagement between the engagement member and the slots. The threaded lockdown collar was tightened and released by rotation about a longitudinal axis on the barrel portion of the device (module). However, the threaded lockdown collar itself was susceptible to loosening under the vibration encountered during the use of the device.

An even further attempt was made to solve the problem by placing a spring-biased button on the device in an effort to help prevent the lockdown collar from turning (loosening) once the lockdown collar was tightened on the engagement member/slot mechanism. The button was situated in a position that would prevent the lockdown collar from rotating unless the button was depressed. This approach required the surgeon to undertake several steps before the orientation of the saw blade mounting mechanism could be adjusted. First, the button needed to be pressed. Next, the lockdown collar needed to be loosened, the distal portion of the barrel rotated, and then the lockdown collar tightened, and finally the button released. During the loosening and tightening of the lockdown collar, the button needed to be depressed. The mechanism was cumbersome in use, resulting in an inconvenient overall design and a relatively complex task to change the orientation of the saw blade.

SUMMARY OF THE INVENTION

The present invention comprises a surgical driver or handpiece having an adjustable barrel portion. The barrel portion includes a tool mount for a surgical tool (e.g. saw blade). A locking mechanism allows the tool mount (and saw blade) to be locked in one of a plurality of positions relative to a proximal portion of the barrel. The present invention may be utilized in both modular and non-modular surgical handpieces.

The present invention provides an adjustable, lockable device that: a) has a feature wherein the position of the surgical tool (e.g. saw blade) may be quickly, easily and conveniently adjusted relative to the proximal end of the barrel of the device, b) can effectively and securely lock the tool in one of a plurality of preselected, indexed positions relative to the proximal end of the barrel of the device without undue vibration of the distal part of the barrel relative to the rest of the barrel, c) can adjust the orientation of the tool and lock it in place without requiring the user to remove or decouple a module and reattach it to the handpiece, d) contributes to the accuracy, precision, versatility and convenience of the drive device, e) can be easily locked and unlocked by manually manipulating a button or lever without requiring the surgeon to screw down a locking collar, and f) is relatively easy to manufacture and is not unduly sensitive to tolerance vagaries.

It is also believed that the performance of the locking mechanism of the present invention is less susceptible to slight changes in tolerances than other locking mechanisms found in the prior art. As a result, the locking mechanism of the present invention may be readily manufactured without undue, close scrutiny of part tolerances.

In one aspect, the present invention comprises a module for a surgical driver. The surgical driver comprises handle and barrel portions with the barrel portion having an axis. The module comprises releasable attachment means for releasably attaching the module to the surgical driver so that the module forms a portion of the barrel portion of the surgical driver. The module also includes tool mounting means for releasably receiving an orthopedic surgical tool, rotational orientation means for orienting the tool mounting means in a plurality of angular positions about the axis of the barrel portion of the surgical driver so that the orthopedic surgical tool may be mounted in a plurality of angular positions relative to the barrel portion of the surgical driver, a unique releasable locking means for releasably locking the rotational orientation means in one of a plurality of angular positions about the axis of the barrel portion of the surgical driver, and biasing means (preferably a spring) for biasing said locking member toward said lock position.

The releasable locking means has a locking member movable between a lock position and a release position spaced from the lock position. The module has a stationary portion which is fixed relative to the barrel portion of the surgical driver, and a movable portion adapted to be rotated relative to the stationaaxis. Preferbout an axis. Preferably, the movable portion of the module comprises a substantially cylindrical sleeve having a plurality of grooves or slots spaced about its periphery. Each of the grooves preferably has a pair of tapered walls.

The releasable locking means affords 360 degree rotation of the movable portion of the device with one of the user's hands while the rest of the device is held and the biasing means is overcome by the user's other hand. The unique locking means simplifies adjustment of the surgical device, while retaining an efficient, secure lock.

In one embodiment of the unique, releasable locking means of the present invention, the locking member comprises a single, eccentric locking member pivotally mounted on the stationary portion of the module. The locking member has a detent with tapered walls that are received in one of the grooves of the cylindrical sleeve.

In another embodiment of the unique locking means of the present invention, the releasable locking means comprises a lever having a ramping recess, and a lock key fixedly attached at one end to the lever and having a detent at another end. The detent has tapered wall surfaces adapted to be received in a slot of a sleeve. A cam is also present with a helical ramped surface for engaging the ramping recess of the lever. The lever is movable between a lock position with the spring biasing means biasing the detent toward engagement with one of the slots and a release position with the detent spaced from the slots. When the lever is moved from the lock to the release position, the helical ramped surface engages the ramping recess and drives the detent from engagement with tapered wall of the slot.

Preferably, the locking member of either embodiment comprises a self-correcting locking member. Several factors may contribute to this feature. For example, the detent may be constructed from a material that is softer than the material forming the grooves of the cylindrical sleeve. The angle between the tapered walls of the grooves may be complementary with the angle between the tapered walls of the detent. Preferably, that angle is between about 2 degrees and about 179 degrees, more preferably, the angle is about 40 degree. Also preferably, the locking member is mounted on the stationary portion so that movement of the detent into the slots is in a direction that is greater than about ten (10) degrees relative to the longitudinal axis of the slot that is receiving the detent, more preferably the direction is substantially perpendicular to the longitudinal axis of the slot.

BRIEF DESCRIPTION OF THE DRAWINGS

FIG. 12 is a side view of a sleeve having a plurality of grooves for use in the first embodiment of locking mechanism according to the present invention;

FIG. 13 is an end view of the sleeve of FIG. 12;

DETAILED DESCRIPTION

Figure 1:
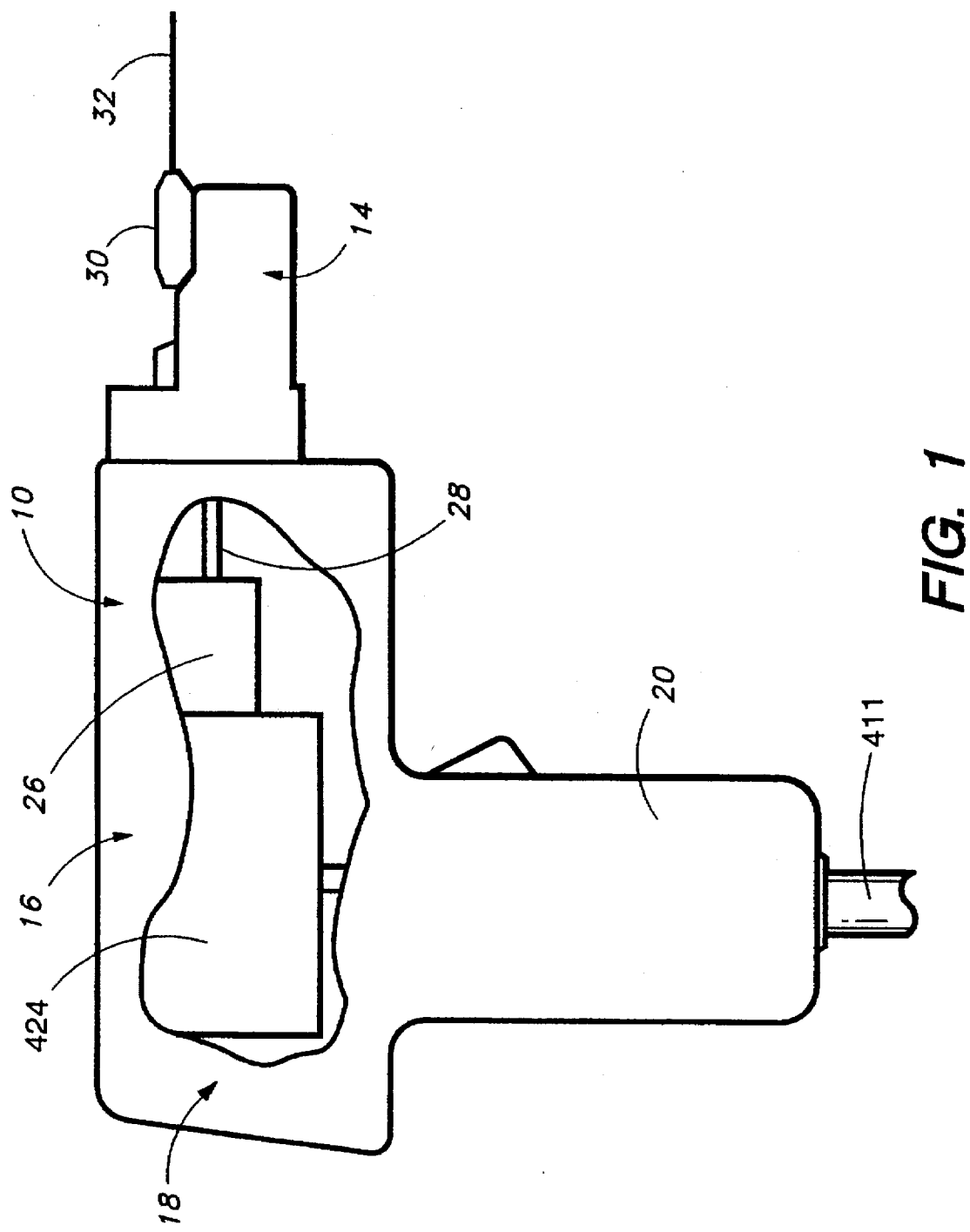
FIG. 1 is a schematic side view of a module and surgical driver according to the present invention.

Referring now to FIG. 1, there is shown a simplified example of a surgical driver 10 and a module 14 for use with the surgical driver 10. The module 14 is constructed to be releasably attached to the surgical driver 10. The handpiece 10 comprises a housing 16, generally divided into a barrel portion 18, and a handgrip or handle portion 20. Preferably, the barrel 18 and handle 20 are situated at an angle relative to one another to form a substantially pistol shaped device. Preferably, the angle between the handle and barrel is less than ninety degrees and more than ten degrees to provide a natural hand position for the surgeon during the various uses of the device 10.

The surgical driver 10 includes a drive means such as a motor 424, a gear system 26 and drive shaft 28. Preferably, the surgical driver 10 comprises a fluid (e.g. pneumatic or gas) driven device which utilizes a fluid inlet 411. Alternatively, the surgical driver 10 may comprise an electrical powered (e.g. battery or cord) device. For example, the surgical driver device 10 may comprise the battery powered handpiece disclosed in commonly assigned U.S. Pat. No. 5,553,675.

The driver 10 is preferably adapted to be connected to and to drive a plurality of orthopedic modules. The orthopedic modules are designed to perform a specific task during an orthopedic surgical procedure. For example, the module 14 may comprise the oscillating or sagittal bone saw module 14 illustrated in FIGS. 1, 2 and 6–8. Alternatively, the module may comprise a module for converting the driver 10 the universal chuck tr driving cutting tools or the reamer driver for use in driving reamers or the like as described in U.S. Pat. No. 4,736,742 (the entire contents of which are herein incorporated by reference). It should be noted that the locking mechanism described below may be incorporated in a variety of different orthopedic modules including those mentioned above and the Reciprocating Saw Attachment (G140A) for the Maxi-Driver 3 Powered Surgical Instrument System available from Minnesota Mining and Manufacturing Co. (3M) of St. Paul, Minn.

Figure 8:
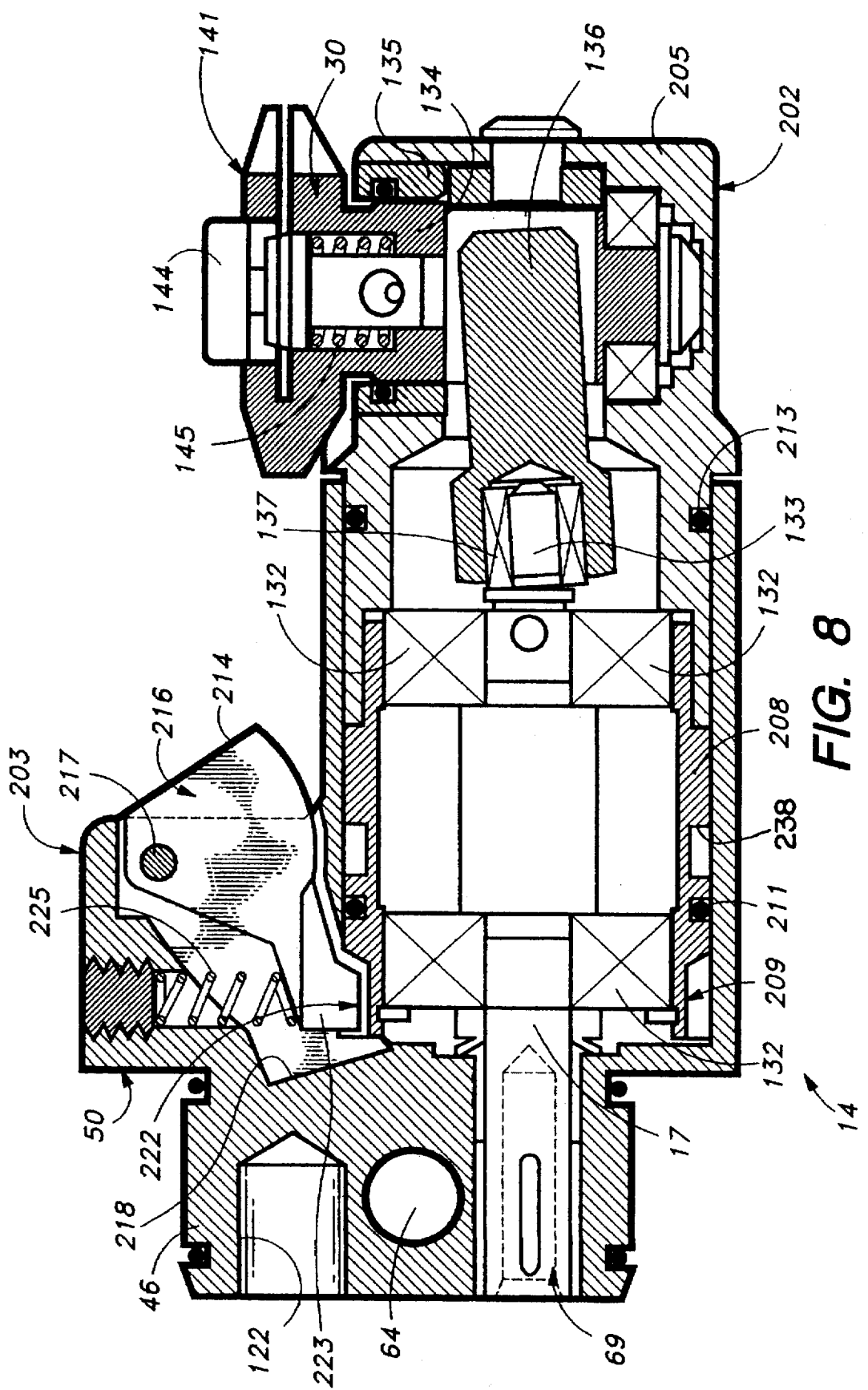
FIG. 8 is an enlarged sectional view of the module of FIG. 7 taken approximately along lines 8—8 of FIG. 7.

Referring to FIG. 8, the module 14 is driven by rotating a driven shaft 17 on the module over a predetermined speed range (e.g. about 15,500 RPM). The module 14 includes a tool mounting means 30 for releasably receiving an orthopedic tool. For the module 14, the tool mounting means 30 is adapted to releasably receive an osteotomy or orthopedic saw blade 32. The tool mounting means are described in greater detail below.

Figure 3:
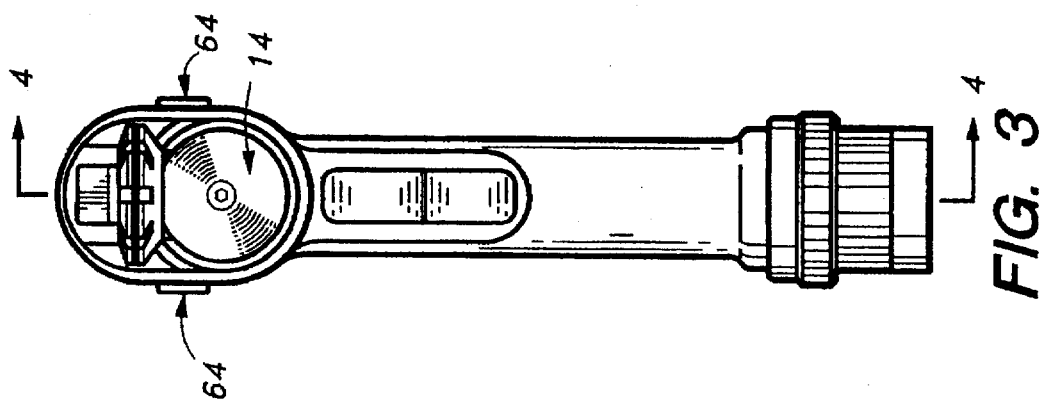
FIG. 3 is a vertical front view of the device and module of FIG. 2.
Figure 2:
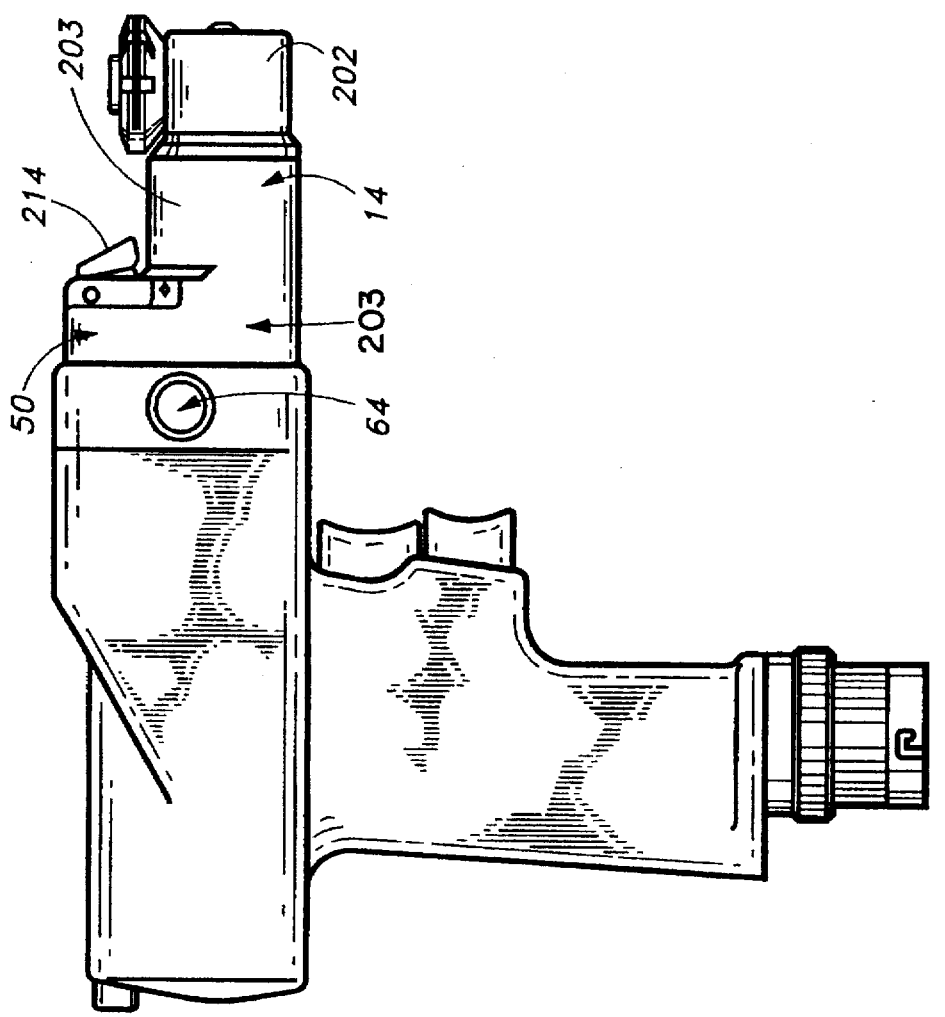
FIG. 2 is a vertical side view of a device according to the present invention with a module in the form of an orthopedic bone saw engaged with the device and with the saw blade omitted for brevity.
Figure 4:
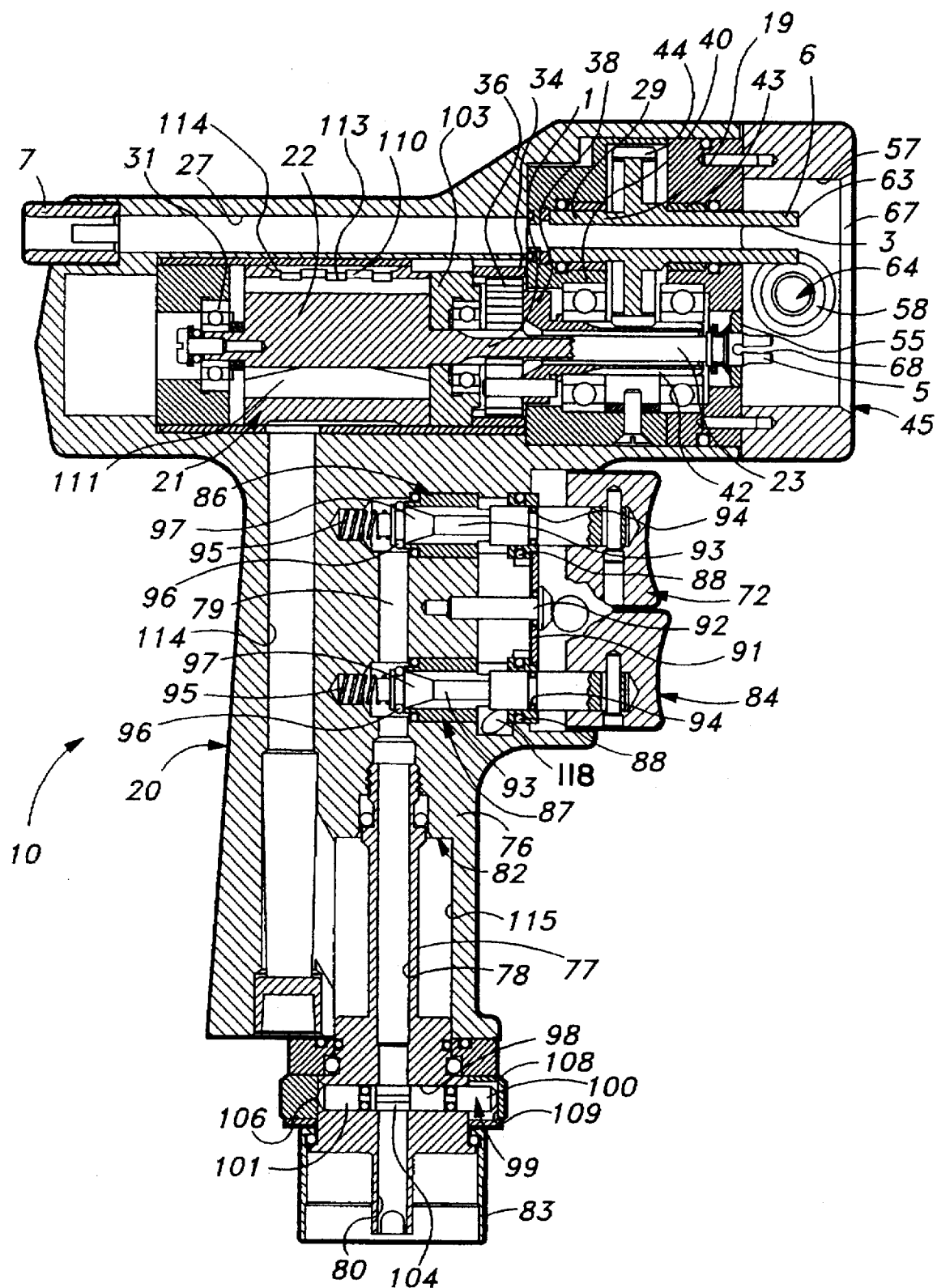
FIG. 4 is an enlarged sectional view taken approximately along lines 4—4 of FIG. 3, but in which the module is omitted to emphasize other details.
Figure 5:
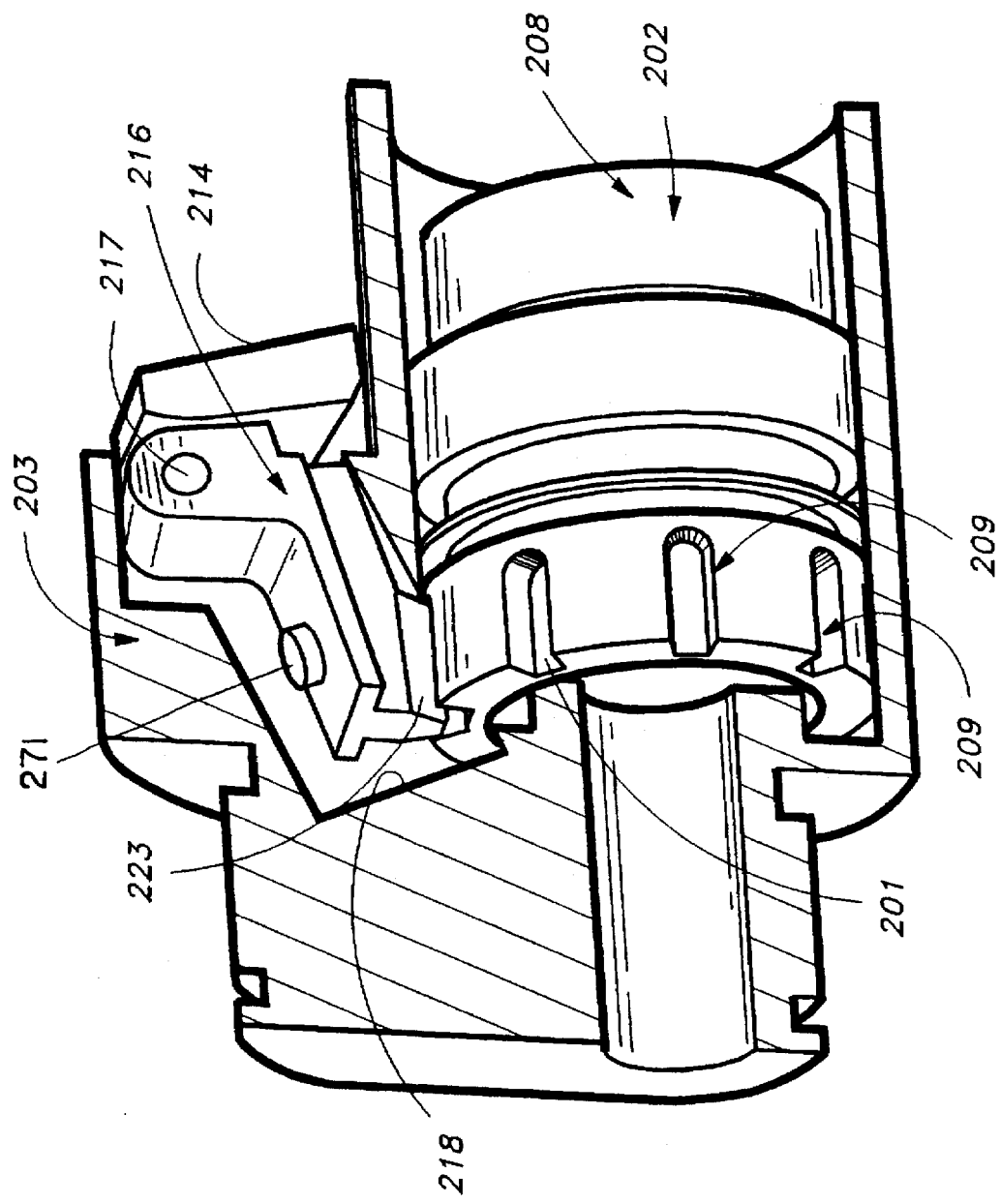
FIG. 5 is a perspective view of a first embodiment of locking mechanism according to the present invention with portions broken away to illustrate internal details of the locking mechanism.
Figure 7:
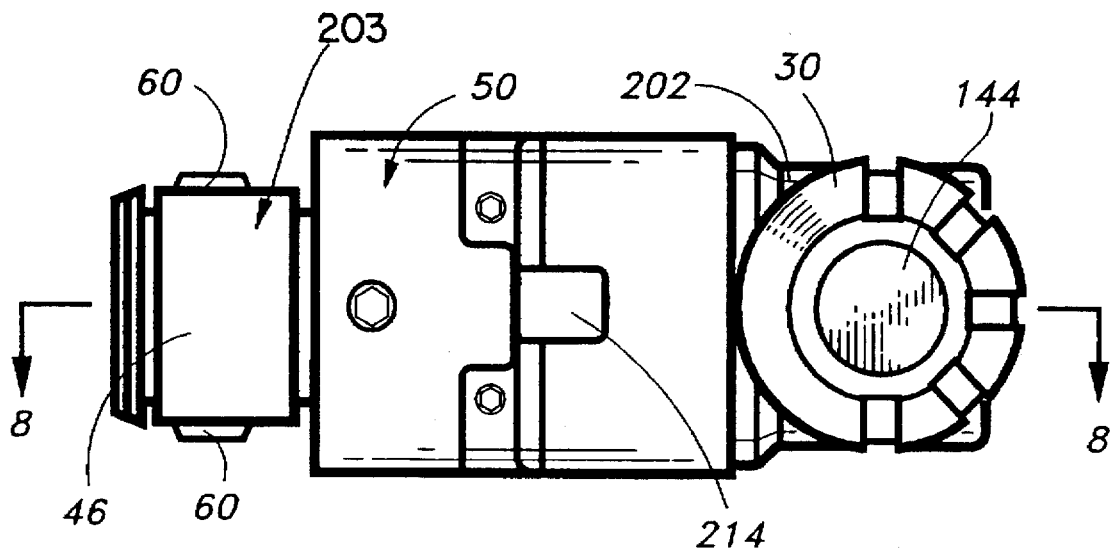
FIG. 7 is a top view of the module of FIG. 6.

FIG. 2–4 illustrate an embodiment of driver 10 which is powered by compressed gas. The driver 10 comprises a frame having a handle portion 20, an air motor 21 mounted on the frame comprising a rotor 22, and first and second spaced axially parallel output shafts 19 and 23 each having an output end portion 5 and 6 adapted to releasably engage the driven shat 17 (FIG. 8) of one of the modules (e.g. 14). The second shah 19 has a through central opening 3 accessible from an end 29 of the second shah 19 opposite its output end 6 through an opening 27 through the frame partially defined by a hard steel cylindrical guide 7.

The driver 10 also includes means for driving the output shafts 19 and 23 from the rotor 22 to rotate both of the output shafts 19 and 23 with the second output shaft 19 rotating at a substantially slower rate of rotation than the first output shaft 23 upon rotation of the rotor 22; releasable attachment means for releasably attaching one of the modules (e.g. 14) to the frame with the driven shaft 17 of the module 14 in driven engagement with the output end 3 or 5 (in the case of the module 14, it is the end 5) of one of the output shafts 19 and 23; and means for coupling a supply of fluid (gas) under greater than atmospheric pressure to the air motor 21 to rotate the rotor 22.

As is best seen in FIG. 4, the means for driving the output shafts 19 and 23 from the rotor 22 includes the first output shaft 23 being fixed to (as by being an integral part of) the rotor 22 and with the rotor 22 being rotatably mounted on the frame by ball bearings 31, a first drive gear I coaxially fixed to (as by being integrally formed with) the first output shaft 23; a ring gear 34 fixed on the frame coaxially around the first drive gear 1; a plurality of planetary gears 36 having teeth engaged with the teeth of the first drive gear I and ring gear 34 around the first drive gear 1; and a carrier 38 having a central opening through which the first output shaft 23 projects. The carrier 38 is rotatably mounted on the frame by ball bearings 40 coaxially about the first output shaft 23. The carrier 38 also rotatably supports the planetary gears 36 in spaced relationship around the first drive gear 1, and has a second drive gear 42 coaxially fixed about (as by being integrally formed on) its periphery. The means for driving the output shafts 19 and 23 from the rotor 22 also includes a driven gear 44 coaxially fixed to (as by being formed on) the second output shaft 19. The driven gear 44 has its teeth in engagement with the teeth of the second drive gear 42.

The second output shaft 19 is rotatably mounted on the frame by spaced sleeve bearings 43.

Releasable attachment means are provided for releasably attaching the module 14 to the frame of the driver 10. As is best seen in FIGS. 3, 4 and 8, when the module 14 is attached to the driver 10, the driven shaft 17 of the module 14 is in engagement with the output end portion 5 of the output shaft 23. The releasable attachment means comprises walls of the frame defining a socket 45 having an inlet opening. The socket 45 is adapted to receive a portion 46 of a frame 50 of the module 14 in close fitting relationship. The walls of the socket 45 include an inner wall defining an inner end surface 55 opposite the socket's inlet opening with the output shafts 19 and 23 projecting through the inner wall and with the output end portions 5 and 6 of the output shafts 19 and 23 being positioned within the socket 45. The socket 45 also includes a side wall 57 fixed to and projecting between the inner end surface 55 and the inlet opening of the socket 45. Preferably, the side wall 57 is a generally oval surface and has opposite end portions that are cylindrically arcuate about the axes of the output shafts 19 and 23.

Figure 6:
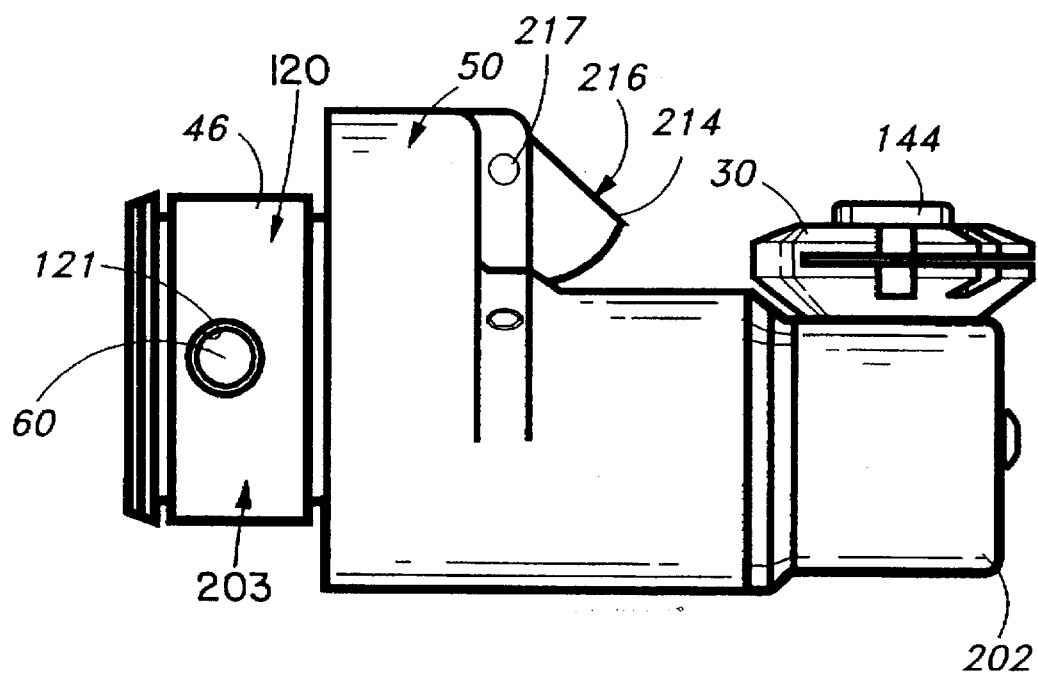
FIG. 6 is a side view of a module utilizing the first embodiment of locking mechanism according to the present invention, which module may be utilized with the surgical driver of FIG. 1 to provide an orthopedic saw.

The releasable attachment means comprise the side wall 57 having opposed transverse stepped through openings 58 adapted to receive locking pins 60 on the module 14 (see FIG. 6). The pins 60 are biased by a spring to project outwardly from that portion of the frame 46 of the module 14 which is adapted to be received in the socket 45. The releasable attachment means include release buttons 64 in the through openings 58 having inner ends adjacent the socket 45 and opposite outer ends accessible from the outer surface of the driver 10. The release buttons 64 are mounted in the through openings 58 for movement between a locking position in which the release buttons 64 are biased by springs and a release position. In the locking position, the inner ends of the buttons 64 are spaced from the side surface 57 of the socket 45 so that the through openings 58 may receive the locking pins 60 of the module 14 to lock the module 14 to the driver 10. The buttons 64 may be moved to the release position by manual engagement with the outer ends of the buttons 64 to press them toward each other at which point the inner ends of the buttons 64 are aligned with the side surface 57 of the socket 45 to remove the locking pins 60 from the through openings 58 so that the module 14 may be separated from the device 10. The side wall 57 is beveled outwardly adjacent the inlet opening of the socket 45 to provide a beveled surface 67 that will act as a lead-in surface to push the outwardly biased locking pins 60 onto the side surface 57 when the frame 46 of the module 14 is inserted into the socket 45.

The output end portion 6 of the second output, shaft 19 comprises two opposed circumferentially spaced tapered projections 63 adapted to engage between two similar shaped spaced tapered projections (not shown) on the ends of the driven shafts of modules other than module 14 (the module 14 does not utilize the output shaft 19). In such an assembly, the tapered ends of the module (other than module 14) cause proper alignment of the shafts as the second output shaft 19 and the driven shaft engage.

The output end portion 5 of the first output shaft 23 has a transverse slot 68 adapted to receive a transverse drive plate 69 (FIG. 8) in the driven shaft 17. The drive plate 69 is slidably mounted in a longitudinal slot diametrically across a socket in the driven shaft 17 and is biased toward the end of the shaft 17 by a spring. The spring affords correction for improper alignment of the output end portion 5 and the drive plate 69 with the slot 68 as the first output shaft 23 is rotated by the device 10.

The means for coupling a supply of fluid (e.g. gas) under greater than atmospheric pressure to the air motor 21 to rotate its rotor 22 comprises: (1) the frame and a pair of plugs (not shown but near reference character 82 in FIG. 4) inserted in openings bored in the frame defining first and second passageways each having inlet ends and having outlet ends in opposite sides of the air motor 21 for directing fluid to different positions so that gas directed through the first passageway into the air motor causes rotation of the rotor 22 in a first or clockwise direction as viewed in FIG. 3, and gas directed through the second passageway into the air motor 21 causes rotation of the rotor 22 in a second direction opposite the first direction or counterclockwise as viewed in FIG. 3; and (2) the frame including a generally tubular portion 77 attached to a main portion 76 of the handle 20 by which the device 10 is manually grasped, and an upper portion in which the air motor 21 and output shafts 19 and 23 are mounted. The tubular portion 77 (FIG. 4) defines the major part of an inlet passageway 78 having an outlet end 79 and an inlet end 80 adapted to be releasably coupled to a source of fluid under pressure such as from a hose 411 (FIG. 1) and a bayonet type quick disconect portion on the hose adapted to engage a mating portion 83 of the quick disconnect rotatably mounted about the tubular portion 77 of the frame.

The means for coupling a supply of fluid (e.g. gas) under greater than atmospheric pressure to the air motor 21 to rotate its rotor 22 also includes main valve means positioned between the outlet end 79 of the inlet passageway 78 and the inlet ends of the first and second passageways (mentioned above) adapted to be activated by manually manipulating a trigger 84 between opened and closed positions for selectively directing fluid from the inlet passageway 78 into one of the first and second passageways. Also, regulating valve means are provided in the inlet passageway 78 between its inlet and outlet ends 80 and 79 which are substantially infinitely adjustable between open and closed positions for regulating the flow of air through the inlet passageway 78.

The main valve means comprises a pair of valve assemblies 86 and 87 each comprising (1) a housing member 88 sealed in the main portion 76 of the frame by O-rings and held in place by a removable plate-like portion 91 of the frame attached to its main portion 76 by a screw 92; and (2) a plunger 93 axially slidably mounted in the housing member 88 and sealed in the housing member 88 by an O-ring 94. The plunger 93 is biased by a spring 95 to a position with an O-ring 96 around a head 97 on the plunger 93 in sealing engagement against a lip on the housing member 88 to prevent fluid at the outlet end 79 of the inlet passageway 78 from passing into the first passageway or the second passageway which the valve assembly 86 or 87 controls. The plungers 93 are movable to an open position by moving the triggers 72 or 84 inwardly relative to the handle 20 to move the plunger 93 and thereby the O-ring 96 on that plunger 93 away from its seat to allow fluid under pressure to pass from the inlet passageway 78 into one of the first or second passageways to produce the desired direction of rotation of the rotor 22. The device 10 also includes a roller (not shown). When one of the triggers (e.g. 84) is depressed, the roller cams into the path of the non-depressed trigger (e.g. 72) to prevent its depression.

The regulating valve means in the inlet passageway 78 comprises walls of the frame portion 77 defining both a part of the inlet passageway 78 and further defining a guide passageway 98 extending transverse of the inlet passageway 78; a spool 99 having end portions 100 and 101 slidably mounted in the guide passageway 98 for longitudinal sliding movement and having O-rings around their peripheries to place them in fluidtight sliding engagement with the frame 77, and a central portion 104 of reduced cross section. The spool 99 is longitudinally slidably in the guide passageway 98 between an on position with the central portion 104 spaced from the inlet passageway 78 and the end portion 100 blocking the inlet passageway 78. Some positions of the spool 99 between its on and off positions restrict flow of gas through the inlet passageway 78. Manually operable means are also present for positioning the spool 99 in any position including its on position and its off position and any position therebetween.

The wall means or portion 77 of the frame defining the inlet passageway 78 and the guide passageway 98 have opposite arcuate outer surfaces 106 with the guide passageway 98 opening through the outer surfaces 106. This feature may be formed, at least in part by a tube screwed into the handpiece. The end portions 100 and 101 of the spool 99 extend to at least the outer surfaces 106. The manually operable means for positioning the spool 99 in any position including its on and its off position and any position therebetween comprises a cam 108 rotatably mounted on the tubular portion 77 of the frame. The cam 108 has cam surfaces 109 adapted for engagement with the end portions 100 and 101 of the spool 99 for moving the spool 99 between its off and on positions upon manual rotation of the cam 108 relative to the frame. The cam 108 also has a knurled cylindrical periphery facilitating manual engagement of the cam 108 to rotate it.

The air motor 21 to which gas may be directed through the first and second passages is of a known type comprising walls defining a generally cylindrical chamber 110 in which the rotor 22 is rotatably mounted about an axis spaced from the axis of the chamber 110. The rotor 22 has a plurality of radially extending slots in which plate-like vanes 111 are slidably positioned and will be biased by fluid pressure (and centrifugal force) in the motor 21 radially outwardly of the rotor 22 into slidable sealing engagement with the inner cylindrical surface defining the chamber 110. Fluid (e.g. gas) directed into the chamber 110 through either the first or second passageways enters through a passageway defined by a plate 103 at the end of the rotor 22 adjacent the output shaft from which a major portion of the gas flows through a crescent shaped cavity into the space between the rotor 22 and chamber 110 and moves with and drives the rotor 22 through about 180 degrees of its rotation where the gas escapes through slots 113 opening at the side of the motor 21 opposite the first and second passageways and through a cavity extending circumferentially around the motor 21 into an exhaust passageway 114 formed in the frame and communicating between the cavity and an outlet opening to the atmosphere adjacent the tubular portion 77 of the frame at the distal end of the handle 20 for the device 10.

Some of the gas (a minor portion of the gas) moves with rotor 22 past the slots 113 and then is exhausted out the crescent shaped cavity (not shown) and the first or second passageway through which pressurized gas is not being introduced to the motor 21. From that passageway, the gas escapes into the housing member 88 of the valve assembly 86 or 87 that is not open between the plunger 93 and housing member 88 of that not open valve assembly 86 or 87 into a passageway defined between the plate-like and main portions 91 and 76 of the frame and through a passageway 118 into a chamber 115 around the tubular portion 77 that communicates with the main exhaust passageway 114.

A first embodiment of module 50 which converts the surgical device 10 into a oscillating bone saw (shown in FIGS. 1–3 and 5–8) comprises its frame, a first part 120 of which has the previously described projecting portion 46 adapted to be received in the socket 45 of the surgical driver handpiece 10. The projecting portion 46 has a transverse opening 121 in which are positioned the locking pins 60 adapted for releasable engagement with the openings 58 in the side wall 57 of the device 10. The pins 60 are movable in the opening in the module 50 within limits determined by engagement of a pin anchored in the module 50 with spaced inner surfaces of the pin 60 defined by a reduced diameter central portion thereof between (1) outer positions at which outer ends of the pins 60 can enter openings 58 to lock the module 50 to the driver 10, and (2) release positions with the pins 60 within the opening in the module 50 at which the projecting portion 46 can be inserted or removed from the device 10. The projecting portions 46 of the module 50 also has a bore 122 adapted to provide clearance for the output end portion 6 of the second output shaft 19 which does not make driving engagement with the orthopedic drive device 10.

The module 14 includes rotational orientation means for orienting the tool mounting means 30 in a plurality of indexed, preselected angular positions about an axis of the barrel portion 18 of the surgical driver 10 so that the orthopedic surgical tool (e.g. the saw blade 32) may be mounted in a plurality of angular positions relative to the proximal end of the barrel portion of the surgical driver 10. The rotational orientation means afford a comfortable grip and operating position for the surgeon regardless of the blade angle required by the particular surgical procedure. The rotational orientation means also contributes to maximum visibility at the surgical site.

The rotational orientation means may comprise module 50 including a stationary portion 203 and a movable portion 202. The movable portion 202 is adapted to be moved relative to the stationary portion 203. The stationary portion 203 includes the projecting portion 46.

The stationary portion 203 is fixed relative to the barrel portion 18 of the surgical driver 10 when the releasable attachment means attaches the module 14 to the driver 10. The movable portion 202 of the bone saw 10 may be rotated 360 degrees to a plurality of preselected, indexed positions relative the stationary portion 203 to present the saw blade 32 at a plurality of orientations with respect to the proximal end of the device 10, as may be convenient during use of the bone saw during surgery.

O-rings 211 and 213 are present to provide fluid isolation and vibration dampening, as well as a surface that movable portion 202 may rotate on. The movable portion 202 may rotate a full 360 degrees on O-rings 211 and 213. A circumferential slot 238 may optionally receive one or more set pins (not shown) to prevent the movable portion 202 from separating from the stationary portion 203.

It is noted that the rotational orientation means enables the saw blade 32 to be rotated relative to the proximal end of the barrel portion 18 without requiring the user to remove the module 50 from the proximal portion of the barrel portion 18. As used herein, when it is said that the rotational orientation means is "independent of the releasable attachment means" it is meant that the saw blade 32 may be rotated relative to the proximal end of the barrel portion 18 without requiring the user to remove or decouple the module 50 from the proximal portion of the barrel portion 18 (e.g. by using sockets 45, opening 58, pins 60 and buttons 64); as opposed to the mechanism of the Mini-Driver drive device and K-120 Sagittal Saw Attachment module which require the decoupling of the module from the rest of the device in order to modify the orientation of the blade.

The driven shaft 17 on the bone saw module 14 is rotatably mounted through a cavity defined in the module 50 by two bearings 132. The driven shaft 17 has an end in the projecting portion 46 carrying a transverse spring that biases drive plate 69. The drive plate 69 is sized and shaped to be engaged by the first output shaft 23 as described above. The driven shaft 17 also has an off-center (eccentric) pin 133 with a central axis. At all rotational positions of the driven shaft 17, the central axis of the off center pin 133 intersects the axis of a drive member 134 mounted in the module 50 by bearing sleeve 135 for pivotal movement about an axis at a right angle to the axis of the driven shaft 17. An orbiting link 136 has a concentric bearing 137 at one end engaged over the off center pin 133, and an opposite flatted end portion (not shown) with flats on both sides parallel to the pivot axis of the driver member 134. The flats on the flatted end portion are closely received in a longitudinally extending slot in the drive member 134. The slot has sufficient length so that the link 136 can pivot in the slot in the plane defined by the axes of the driven shaft 17 and drive member 134. Thus the movement of the axis of the link 136 out of that plane will cause movement of the drive member 134; that movement being an oscillating movement of the drive member 134 about its axis as the driven shaft 17 is rotated by the device 10.

The drive member 134 is included in a tool mount or attaching assembly 141 for releasably attaching an osteotomy or other surgical saw blade 32. The attaching assembly 141 and blade 32 are more completely described in U.S. Pat. No. 4,386,609 and U.S. patent application Ser. No. 08/469,807 (incorporated herein by reference). As described more fully in U.S. Pat. No. 4,386,609, the blade 32 can be inserted or removed by depressing a locking button 144 included in the attaching assembly 141 against the bias of a spring 145.

The movable portion 202 of the module 14 preferably has the tool mounting means 30 movably attached to a base member 205 thereof so that the saw blade may oscillate relative to the movable portion 202. The base member 205 is fixedly attached to a substantially cylindrical, grooved sleeve 208 which is best shown in FIGS. 12 and 13. The sleeve 208 has a plurality of tapered grooves or slots 209 that are indexed about sleeve 208 in increments of about 45 degree angles.

The module 14 also includes a releasable locking means for releasably locking the rotational orientation means in one of a plurality of discrete angular positions about an axis of the barrel portion 18 of the surgical driver 10. Unlike some prior art devices, the releasable locking means of the present invention comprises a device capable of securely holding the movable portion 202 in position relative to the stationary portion 203 during use of the saw blade 32 (even when significant vibration is encountered). The locking mechanism of the present invention enhances the ability of the device to accomplish accurate, exact, precision surgical procedures, yet is relatively easy to manufacture and repair.

The axis about which the rotation of the barrel portion 18 occurs need not be the central longitudinal axis of the barrel portion 18 or even the central longitudinal axis of the movable portion 202. The axis may be any axis drawn along any portion of the barrel portion 18. Preferably, the axis about which the locking means locks the rotational orientation means is the longitudinal axis of the substantially cylindrical sleeve 208.

The releasable locking means shown in FIG. 8 comprises a locking member 216. A pin 217 extends through hole 219 and pivotally mounts portions of the eccentric locking member 216 within a cavity 218 in the stationary portion 203. Preferably, the cylindrical hole 219 is located at a position other than the geometric center of the locking member 216 so that the locking member 216 comprises an eccentric locking member.

The locking member 216 also includes a tapered detent 222 with tapered side walls 223, and elongate arm portion 229. The tapered detent 222 is preferably complementary to the taper of the slots 209 (theta, see FIG. 13) of the sleeve 208. Preferably the taper of the slots 209 is approximately equal to the angle between the side walls 223 of the detent. The angle should be chosen to provide enough surface contact between the walls 223 and the slot 209 for a sufficiently secure lock, but not one in which the engagement between the walls 223 and slot 209 becomes difficult to break. Also preferably, the angle should provide a self releasing taper, this is, the angle (e.g. theta) should be greater than about 2 degrees and less than about 179 degrees to help ensure that a user may readily disengage the contact between the detent 222 and the slot 209 with a reasonable amount of force, yet provide sufficient surface area contact between the walls 223 and the slot 209 to provide for a secure lock. More preferably, the angle should be between about 30 degrees and about 60 degrees, with the most preferred angle being about 40 degrees.

As an example not intended to be limiting, for a sleeve 208 with an outer diameter of about 1.137 inches, a length of about 1.25 inches, and a minimum inner diameter of about 0.85 inches, if the taper (theta) of the slots 209 is approximately forty degrees (see FIG. 13), the depth of the slot 209 is about 0.09 inches, the width of the slot is about 0.140 inches, and the length of the slot is about 0.26 inches; then the angle between the side walls 223 of the detent should be about forty (40) degrees. The thickness of the detent 222 at the beginning of the taper of the walls 223 may be about 0.18 inches tapering to a thickness of about 0.92 inches. Alternatively, the taper (the angle between the side walls) of the detent 222 may be slightly larger than the taper (theta) of the slots 209 in order to resist engagement between the tapered detent and the bottom walls 201 of the slot 209.

Figure 9:
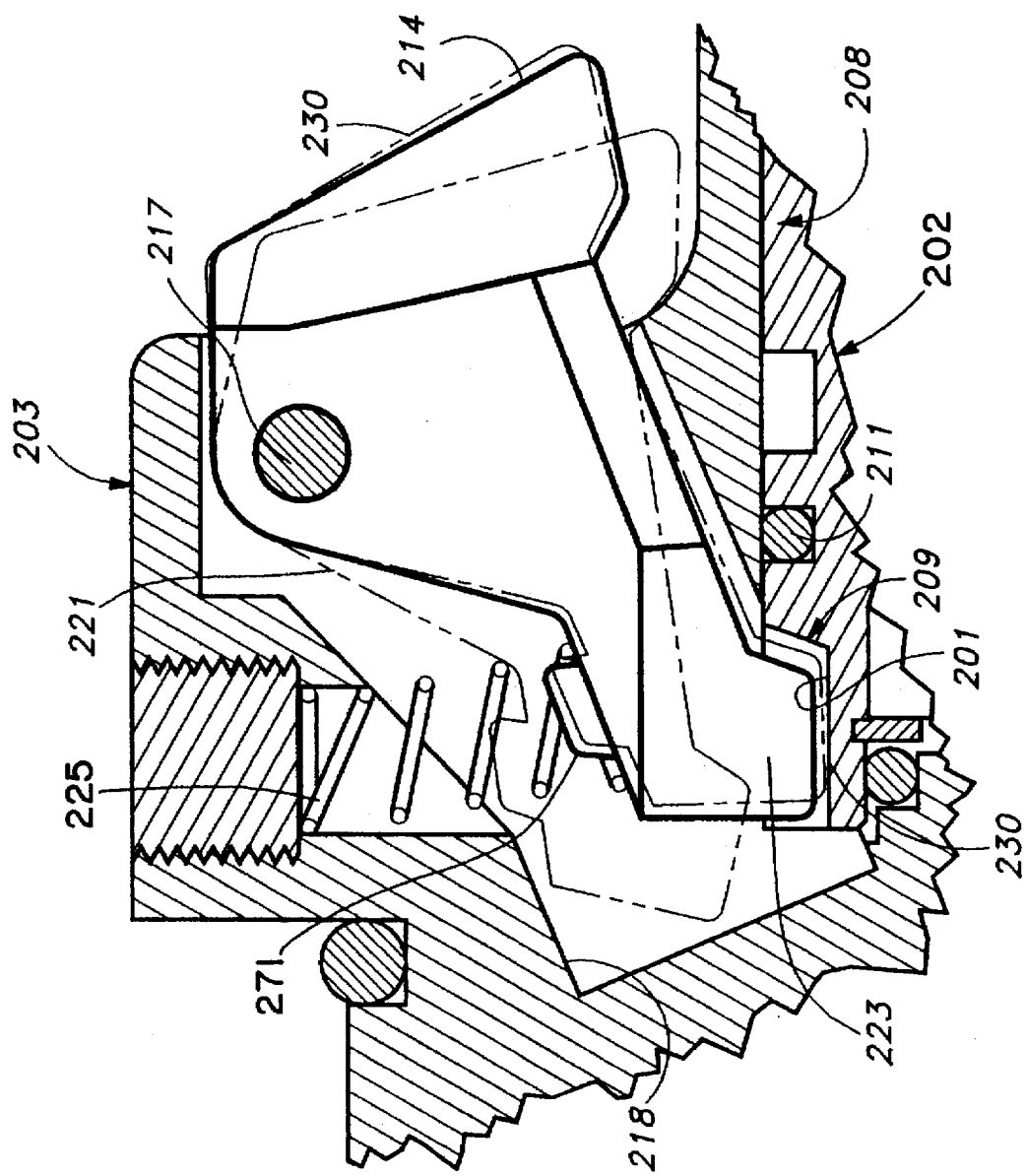
FIG. 9 is a sectional view of portions of the first embodiment of locking mechanism according to the present invention, which illustrates an eccentric locking element in (1) a locking position with solid lines, (2) a release position with a first set of dashed (hidden) lines and (3) a partially worn position with a second set of dashed (hidden) lines.
Figure 11:
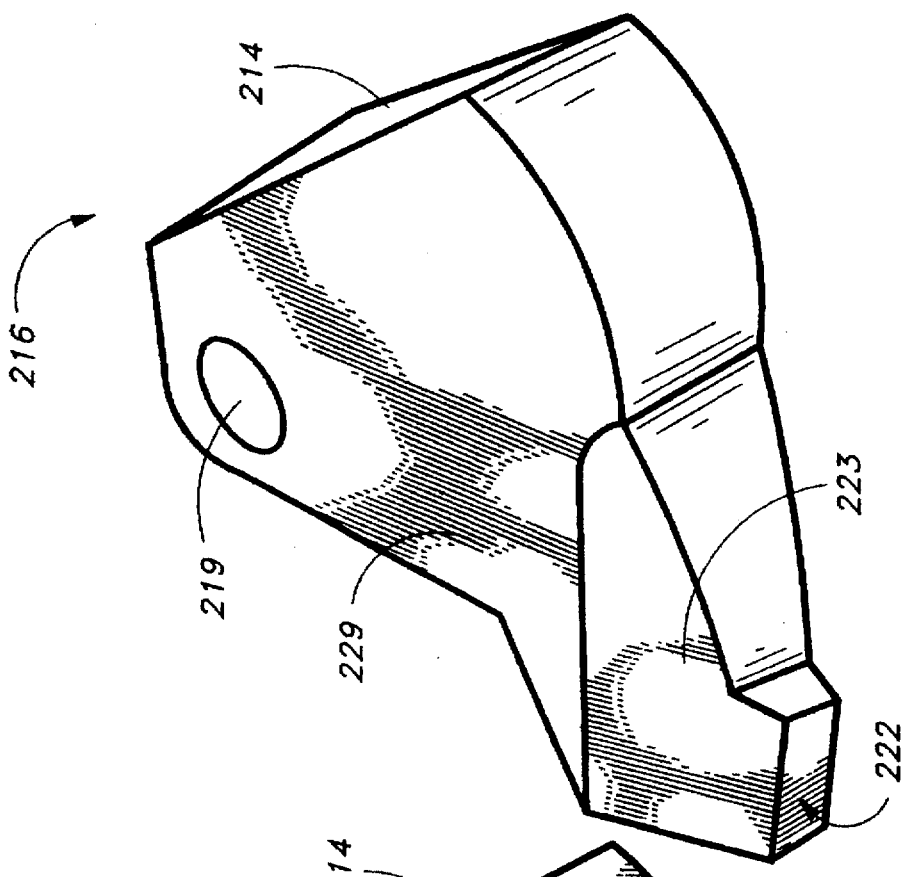
FIG. 11 is another perspective view of the eccentric locking element of FIG. 10 illustrating the eccentric locking element from a different perspective than the perspective of FIG. 10.
Figure 10:
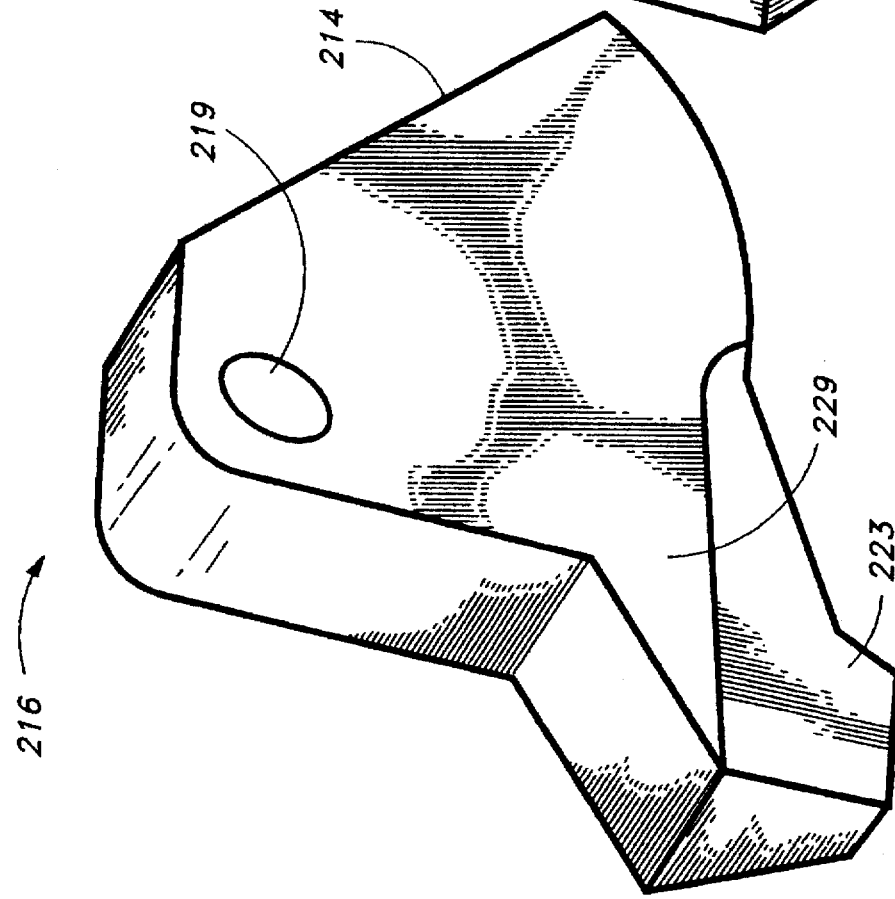
FIG. 10 is a perspective view of an eccentric locking element of the first embodiment of locking mechanism with a spring stop feature of the device removed to emphasize other details.
Figure 14:
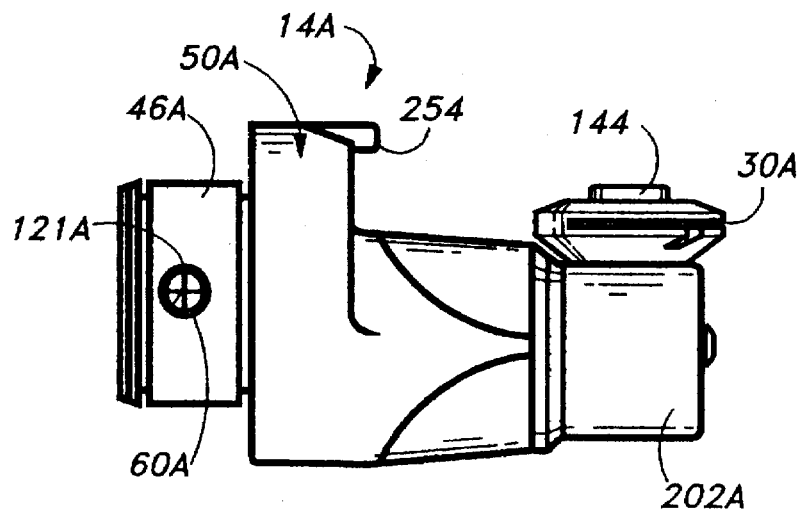
FIG. 14 is a side view of a second embodiment of a module according to the present invention which utilizes a second embodiment of a locking mechanism.
Figure 15:
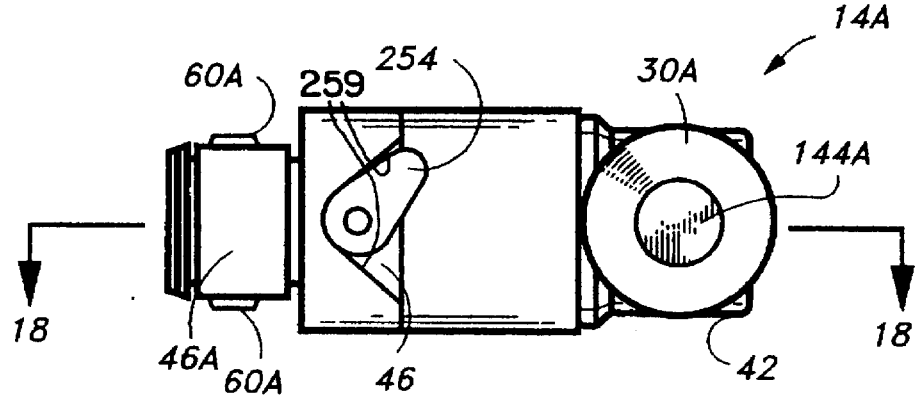
FIG. 15 is a top view of the module of FIG. 14.

Referring now to FIG. 9, the locking member 216 is pivotally mounted to the stationary portion 203 for movement between a lock position (solid lines) with the side walls 223 of the detent 222 engaged with the tapered walls of the slot 209, and a release position (dashed lines 221) with the detent 222 spaced from the slot 209 such that the sleeve 208 may be rotated relative to the stationary portion 203.

A compression spring 225 is mounted between the stationary portion 203 and the detent 222 of the locking member 216. The spring 225 biases the locking member 216 toward the locking position. The detent 222 preferably includes a spring stop or center 271 for retaining one end of the spring 225 on the detent 222.

Preferably, the direction of the bias provided by the spring 225 is other than along the axis of rotation of the movable portion 202. More preferably, the direction of the bias provided by the spring 225 is substantially perpendicular to the axis of rotation of the movable portion 202.

A user may move the locking member 216 from the locking position toward the release position by pressing on manually engagable surfaces 214 of the locking member 216. Because the pin 217 mounts the eccentric locking member 216 in a position other than the geometric center of the locking member 216, a mechanical advantage may be used to manually overcome the bias of the spring 225. It should be noted that the present invention allows the user to hold the device 10 and overcome the bias of the spring 225 with one hand, and use the other hand to rotate the movable portion 202, as opposed to prior art devices (such as the Stryker 2108 sagittal saw) which encourage the use of the hand nearest the saw blade to both overcome the bias of a spring and to rotate the distal portion of the barrel of the device. With the present invention, the user's hand nearest to the saw blade 32 has a relatively simple task to perform and is not burdened by the further task of overcoming the force of the spring 225. Instead, the hand holding the device 10 overcomes the spring bias 225.

Engagement between the detent 222 and the slot 209 locks the movable portion 202 in an angular position relative to the stationary portion 203. A plurality of slots 209 (preferably eight) allows the movable portion 202 to be indexed to a plurality of positions relative to the stationary portion 203. In this manner the tool mount 30 and the tool 32 may be locked in a plurality of orientations relative to the barrel portion 18 of the device 10.

While the locking means (which includes the eccentric locking member 216 and slots 209) are illustrated with respect to module 14 for use with the driver 10, the locking means illustrated in FIGS. 5-11 could be readily utilized in a non-modular surgical device. For example, simply removing the releasable attachment means and fixing the stationary portion 203 to the barrel portion 18 of the surgical device 10 would render the device 10 a non-modular surgical device.

Preferably the locking member 216 comprises a self-correcting locking member to account for wear. To securely lock the movable portion 202 relative to the stationary portion 203, the locking member 216 should retain contact between the tapered side walls 223 of the detent 222 and the tapered walls of the slot 209.

The slots 209 have longitudinal axis A (FIG. 12). Preferably, the angle that the tapered side walls 223 enter the slots 209 relative to the axis A should be greater than ten (10) degrees to contribute to a self-correcting feature of the locking member 216 of the present invention. A variety of factors affect the angle with which the tapered side walls 223 enter the slots 209. For example, the various dimensions of the locking member 216, the eccentricity of the locking member 216, the relative positions of the sleeve 208 and the locking member 216. Preferably, in order to contribute to the self-correcting feature of the locking member 216, movement of the tapered surfaces of the detent portion 222 into and out of the slot 209 should be substantially perpendicular to the longitudinal axis A of the tapered slot 209. This relative motion of the locking member 216 and slot 209 is also believed to contribute to the ease with which engageinent between the tapered walls 223 and the slot 209 is broken, while maintaining a secure engagement between the walls 223 and the slot 209.

The self-correcting feature of the locking member 216 is illustrated in FIG. 9. Dashed lines 230 illustrate the position of the detent 222 after the slot 209 has become slightly worn. As the walls 223 wear, the detent member 222 is designed to sink deeper into the slot 209 to maintain contact between the side walls of the slot 209 and the side walls 223 of the detent 222. As the detent member 222 sinks deeper into the slot 209, parts of the tapered walls 223 which were not previously in contact with the slot 209 begin to contact the walls of the slot 209 to maintain the secure lock, in spite of the wear.

Preferably the detent 222 is constructed from a material that is slightly softer than the material used to construct the slots 209 to help provide the self-correcting feature of the locking member 216. This is also preferable as the detent 222 is generally easier to replace than the sleeve 208. For example, the sleeve 208 may be constructed from a 440 C stainless steel that is heat treated to a Rockwell C hardness between about 56 and 60, while the detent 222 may be constructed from a 420 stainless steel that is heat treated to a Rockwell C hardness between about 48 and 53.

FIGS. 14–20 illustrate portions of a second embodiment of a module for use with a surgical driver according to the present invention generally designated by reference character 14A. The module 14A has many elements which are similar to the elements of the module 14. Elements in the module 14A which are the same or very similar to the elements in the module 14 have been given the same reference character as their counterparts in module 14, to which the suffix "A" has been added.

Figure 19:
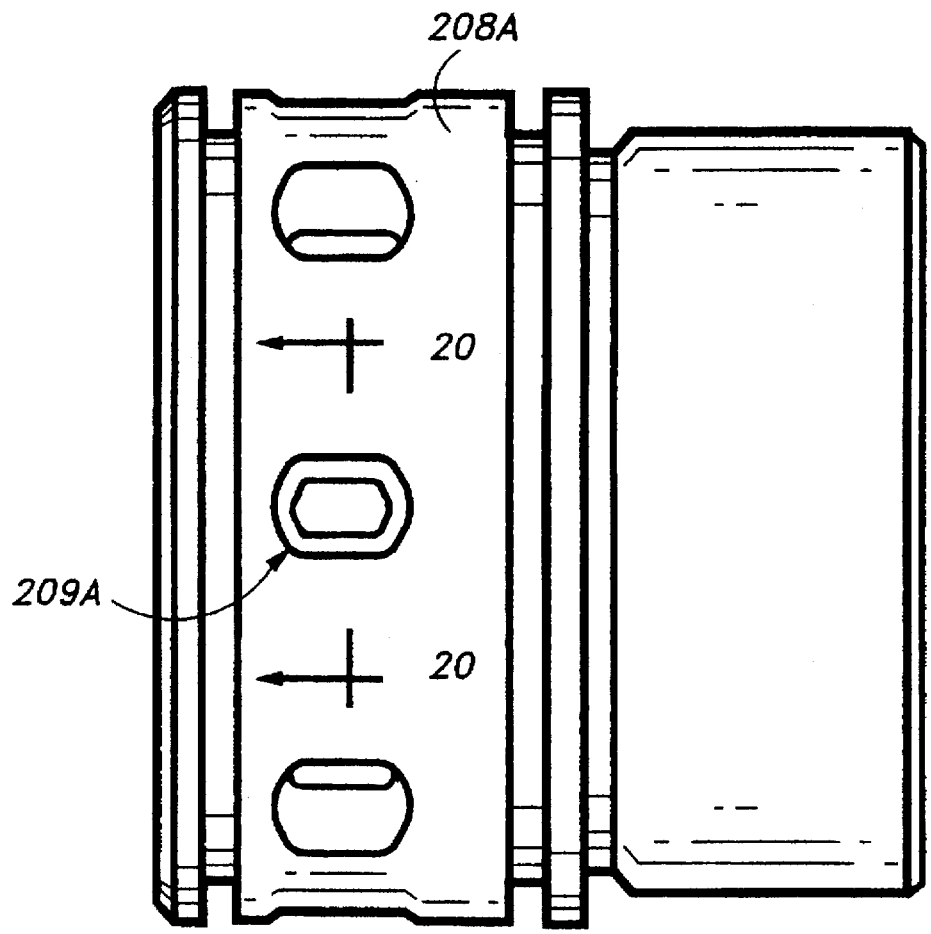
FIG. 19 is a side view of a sleeve having a plurality of grooves for use in the second embodiment of locking mechanism according to the present invention.
Figure 20:
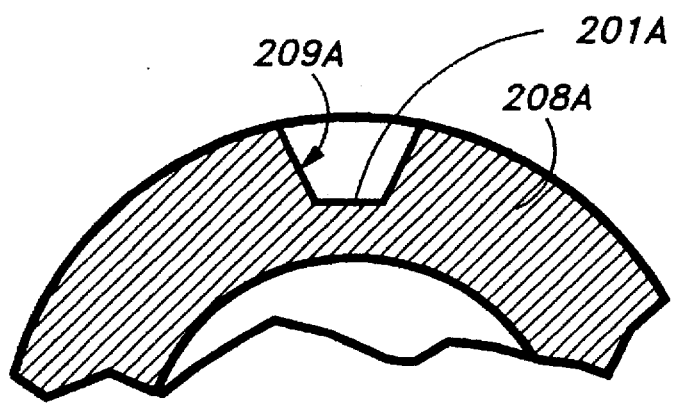
FIG. 20 is an end view of the sleeve of FIG. 19.

In the module 14A, the releasable locking means for releasably locking the rotational orientation means in one of a plurality of discrete angular positions about the axis of the barrel portion of the surgical driver is different than the locking means for the module 14. Referring now to FIGS. 19 and 20, there is shown a sleeve 208A with a plurality of slots 209A with bottom walls 201A. Unlike the open ended slots 209 in the sleeve 208, the slots in the sleeve 208A are closed at each end.

Figure 16:
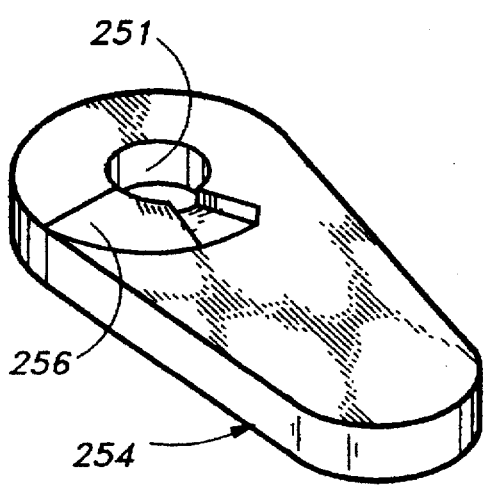
FIG. 16 is a perspective view of a lever used to raise a locking pin of the second embodiment of locking mechanism of FIG. 14.
Figure 17:
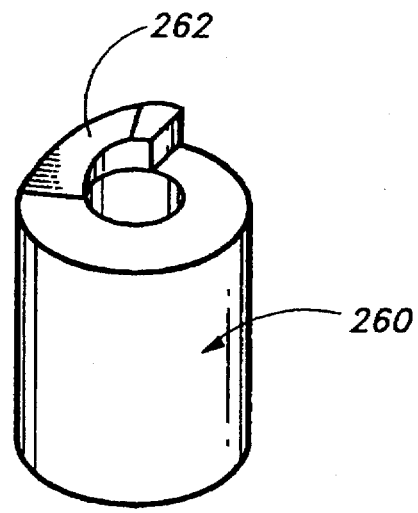
FIG. 17 is a perspective view of a ramped insert which is cooperative with the lever of FIG. 16.
Figure 18:
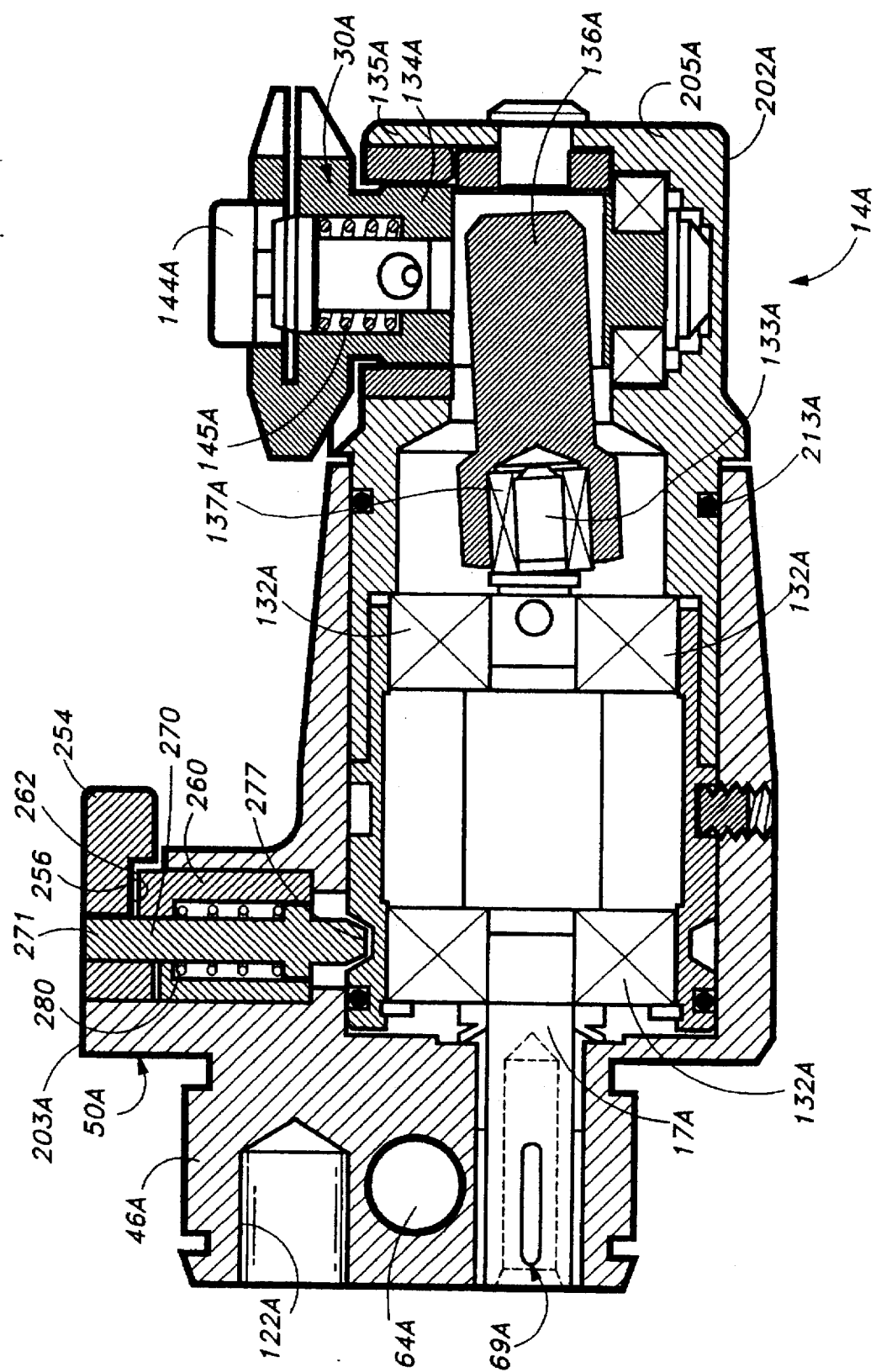
FIG. 18 is an enlarged cross-sectional view of the second embodiment of module of FIG. 15, taken approximately along lines 18—18 of FIG. 15.

The locking mechanism of the module 14A comprises a lever 254 which is pivotally mounted to the stationary portion 203A of the module housing. As best seen in FIG. 16 which illustrates the underside of the lever 254, the lever 254 has a ramping recess 256. The locking means includes a cam 260 having a helical ramped surface 262 that is complementary to ramping recess 256. The locking mechanism also includes a pawl or lock key 270 which has one end 271 fixedly attached to the lever 254 within a hole 251 in the lever 254. The locking mechanism includes a detent 277 at the end opposite of the end 271.

The detent 277 is sized and shaped to be received in one of the slots 209A of the sleeve 208A to resist movement of the movable portion 202A of the module 14A relative to the stationary portion 203A. The lock key 270 and lever 254 are mounted on the stationary portion 203A for movement between a locking position with the detent 277 engaged with a slot 209A of the sleeve 208A (FIG. 18) and a release position with the detent 277 spaced from the slot 209A (and with the lever 254 raised slightly above its position shown in FIG. 18) so that the movable portion 202A may rotate relative to the stationary portion 203A.

A spring 280 biases the lock key 270 toward the locking position. Pivoting the lever 254 relative to the stationary portion of the housing 203A causes the surfaces 262 and 256 to engage and cam (move) the key 270 and lever 254 toward the release position. In particular, when the lever 254 is moved from the locking toward the release position, surface 256 travels up surface 262 thereby lifting the detent 277 out of the slot 209A allowing the sleeve 209A to be rotated. Stop surfaces 259 on the stationary portion 203A prevent the movement of the lever 254 much beyond the release and lock positions.

The lever 254 is movable between a lock position (FIG. 18) with the spring 280 biasing the detent 277 toward engagement with one of the slots 209A and a release position with the detent 277 spaced from the slot 209A. When the lever 254 is moved from the lock to the release position, the helical ramped surface 262 engages the ramping recess 256 and drives the detent 277 from engagement with tapered wall of the slot 209.

Unlike the module 14 which requires the button 214 to be constantly pressed in order to move the locking member 216 to the release position, in the module 14A, movement of the lever 254 from the locking to the release position overcomes the bias of the spring 280 and a user need not keep a finger on the lever 254 in order to retain the detent 277 in a release position. Holding surfaces near surfaces 256 and 262 engage each other and hold the lever 254 in the release position against the bias of spring 280. This simplifies the procedure in that a user need not constantly overcome the bias of a spring while rotating the distal portion of the barrel to the desired location.

The present invention has now been described with reference to several embodiments thereof. It will be apparent to those skilled in the art that many insubstantial changes or additions can be made in the embodiments described without departing from the scope of the present invention. For example, the locking mechanisms of the present invention have been shown in conjunction with a pistolshaped device. The locking mechanisms of the present invention may be readily incorporated in non-pistol-shaped surgical devices in order to gain the secure locking features of the present invention. Thus, the scope of the present invention should not be limited to the structures described in this application, but only by structures described by the language of the claims and the equivalents of those structures.

We claim:

1. A module for a surgical driver with at least one drive shaft, said surgical driver comprising a handle portion and a barrel portion, the module comprising:

releasable attachment means for releasably attaching the module to the surgical driver so that the module forms a portion of the barrel portion of the surgical driver, tool mounting means for releasably receiving an orthopedic surgical tool;

means for engaging the at least one drive shaft, rotational orientation means, independent of said releasable attachment means, for orienting the tool mounting means in a plurality of angular positions about an axis of the barrel portion of the surgical driver so that the orthopedic surgical tool is capable of being mounted in a plurality of angular positions relative to the barrel portion of the surgical driver, releasable locking means for releasably locking the rotational orientation means in one of a plurality of discrete angular positions about the axis of the barrel portion of the surgical driver, said releasable locking means having a locking member movable between a lock position and a release position spaced from the lock position in a direction other than along the axis of the barrel portion, and spring biasing means for biasing said locking member toward said lock position.

2. A module according to claim 1 wherein the module comprises a stationary portion which is fixed relative to the barrel portion of the surgical driver when the releasable attachment means attaches the module to the surgical driver, and a movable portion adapted to be moved relative to the stationary portion.

3. A module according to claim 2 wherein the movable portion of the module comprises a substantially cylindrical sleeve having a plurality of grooves spaced about its periphery, each of said grooves having a pair of tapered walls, the locking member comprises a single, eccentric locking member pivotally mounted on the stationary portion of the module, the locking member having a detent with tapered walls that are sized and shaped to be received in one of the grooves of said cylindrical sleeve when said locking member is in said lock position.

4. A module according to claim 3 wherein the locking member comprises a self-correcting locking member.

5. A module according to claim 4 wherein the grooves of the cylindrical sleeve are constructed from a material, and the detent is constructed from a material that is softer than the material of the grooves of the cylindrical sleeve.

6. A module according to claim 4 wherein the tapered walls of the grooves form an angle therebetween, the tapered walls of the detent form an angle therebetween, and the angle between the tapered walls of the grooves is complementary with the angle between the tapered walls of the detent.

7. A module according to claim 6 wherein the angle between the tapered walls of the grooves and the angle between the tapered walls of the detent is between about 2 degrees and about 179 degrees.

8. A module according to claim 7 wherein the angle between the tapered walls of the grooves and the angle between the tapered walls of the detent is about forty degrees.

9. A module according to claim 2 wherein the releasable locking means affords rotation of the movable portion with one of the user's hands while the spring biasing means is overcome by the user's other hand.

10. A module according to claim 2 wherein the movable portion of the module comprises a substantially cylindrical sleeve having a plurality of slots spaced about its periphery, each of said slots having a longitudinal axis and a pair of tapered walls, the locking member comprises a detent with tapered walls that are sized and shaped to be received in one of the slots of said cylindrical sleeve when said locking member is in said lock position, and wherein said locking member is mounted on said stationary portion so that movement of the detent into the slots is in a direction that is greater than about ten (10) degrees relative to the longitudinal axis of the slot that is receiving the detent.

11. A module according to claim 10 wherein the movement of the detent into the slots is in a direction that is substantially perpendicular to the longitudinal axis of the slot that is receiving the detent.

12. A module according to claim 10 wherein the releasable locking means comprises a lever having recess, a lock key fixedly attached at one end to said lever and having a detent at another end, said detent having tapered wall surfaces sized and shaped to be received in a slot of said sleeve, and a cam having a helical ramped surface for engaging the ramping recess of said lever, said lever being movable between a lock position with the spring biasing means biasing said detent toward engagement with one of said slots and a release position with said detent spaced from said slots; and wherein when the lever is moved from said lock to said release position, said helical ramped surface engages the ramping recess and drives said detent from engagement with the tapered wall of the slot.

13. A module for a surgical driver with at least one drive shaft, said surgical driver comprising a handle portion and a barrel portion, the module comprising:

releasable attachment means for releasably attaching the module to the surgical driver so that the module forms a portion of the barrel portion of the surgical driver, tool mounting means for releasably receiving an orthopedic surgical tool;

means for engaging the at least one drive shaft, rotational orientation means for orienting the tool mounting means in a plurality of angular positions about an axis of the barrel portion of the surgical driver so that the orthopedic surgical tool is capable of being mounted in a plurality of angular positions relative to the barrel portion of the surgical driver, releasable locking means for releasably locking the rotational orientation means in one of a plurality of discrete angular positions about the axis of the barrel portion of the surgical driver, said releasable locking means having a locking member movable between a lock position and a release position spaced from the lock position, a stationary portion adapted to be fixed relative to the barrel portion of the surgical driver when the releasable attachment means attaches the module to the surgical driver, and a movable portion comprising a substantially cylindrical sleeve having a plurality of slots spaced about its periphery, each of said slots having a longitudinal axis and a pair of tapered walls, said movable portion being adapted to rotate about an axis of the sleeve, the locking member comprising a detent with tapered walls that are sized and shaped to be received in one of the slots of said cylindrical sleeve when said locking member is in said lock position; and spring biasing means for biasing said locking member toward said lock position.

14. A module according to claim 13 wherein the locking member comprises a self-correcting locking member.

15. A module according to claim 14 wherein the slots of the cylindrical sleeve are constructed from a material, and the detent is constructed from a material that is softer than the material of the slots of the cylindrical sleeve, the tapered walls of the slots form an angle therebetween, the tapered walls of the detent form an angle therebetween, and the angle between the tapered walls of the slots is complementary with the angle between the tapered walls of the detent.

16. A module according to claim 13 wherein the releasable locking means affords rotation of the movable portion with one of the user's hands while the spring biasing means is overcome by the user's other hand.

17. A module according to claim 13 wherein each of said slots of said cylindrical sleeve have a longitudinal axis, and wherein said locking member is mounted on said stationary portion so that movement of the detent into the slots is in a direction that is greater than about ten (10) degrees relative to the longitudinal axis of the slot that is receiving the detent.

18. A module according to claim 17 wherein the movement of the detent into the slots is in a direction that is substantially perpendicular to the longitudinal axis of the slot that is receiving the detent.

19. A module according to claim 13 wherein:

the releasable locking means comprises a lever having a ramping recess, a lock key fixedly attached at one end to said lever and said detent at another end, and a cam having a helical ramped surface for engaging the ramping recess of said lever, said lever being movable between a lock position with the spring biasing means biasing said detent toward engagement with one of said slots and a release position with said detent spaced from said slots; and wherein when the lever is moved from said lock to said release position, said helical ramped surface engages the ramping recess and drives said detent from engagement with the tapered wall of the slot.

20. A non-modular orthopedic saw comprising:

a barrel portion having an axis, a handle portion situated at an angle relative to said barrel portion, blade mounting means for releasably receiving an orthopedic saw blade, said blade mounting means being situated on said barrel portion, rotational orientation means for orienting the blade mounting means in a plurality of angular positions about the axis of the barrel portion of the saw so that the orthopedic saw blade is capable of being mounted in a plurality of angular positions relative to the barrel portion of the saw, releasable locking means for releasably locking the rotational orientation means in one of a plurality of angular positions about the axis of the barrel portion of the saw, said releasable locking means having a locking member movable between a lock position and a release position spaced from the lock position, a stationary portion adapted to be fixed relative to the barrel portion of the saw, and a movable portion comprising a substantially cylindrical sleeve having a plurality of slots spaced about its periphery, each of said slots having a longitudinal axis and a pair of tapered walls, said movable portion being adapted to rotate about an axis of the sleeve, the locking member comprising a detent with tapered walls that are sized and shaped to be received in one of the slots of said cylindrical sleeve when said locking member is in said lock position; and spring biasing means for biasing said locking member toward said lock position.

21. A saw according to claim 20 wherein the locking member comprises a self-correcting locking member.

22. A saw according to claim 21 wherein the slots of the cylindrical sleeve are constructed from a material, and the detent is constructed from a material that is softer than the material of the slots of the cylindrical sleeve, the tapered walls of the slots form an angle therebetween, the tapered walls of the detent form an angle therebetween, and the angle between the tapered walls of the slots is complementary with the angle between the tapered walls of the detent.

23. A saw according to claim 20 wherein the releasable locking means affords rotation of the movable portion with one of the user's hands while the spring biasing means is overcome by the user's other hand.

24. A saw according to claim 20 wherein each of said slots of said cylindrical sleeve has a longitudinal axis, and wherein said locking member is mounted on said stationary portion so that movement of the detent into the slots is in a direction that is greater than about ten (10) degrees relative to the longitudinal axis of the slot that is receiving the detent.

25. A module according to claim 24 wherein the movement of the detent into the slots is in a direction that is substantially perpendicular to the longitudinal axis of the slot that is receiving the detent.

26. A module according to claim 20 wherein:

the releasable locking means comprises a lever having a ramping recess, a lock key fixedly attached at one end to said lever and said detent at another end, and a cam having a helical ramped surface for engaging the ramping recess of said lever, said lever being movable between a lock position with the spring biasing means biasing said detent toward engagement with one of said slots and a release position with said detent spaced from said slots; and wherein when the lever is moved from said lock to said release position, said helical ramped surface engages the ramping recess and drives said detent from engagement with the tapered wall of the slot.

* * * * *